(12) United States Patent
Baran et al.

(10) Patent No.: US 9,464,087 B2
(45) Date of Patent: Oct. 11, 2016

(54) DIFLUOROMETHYLATION OF UNSATURATED COMPOUNDS

(71) Applicant: The Scripps Research Institute, La Jolla, CA (US)

(72) Inventors: Phil S. Baran, San Diego, CA (US); Janice Akemi Dixon, Dallas, TX (US); Ryan Baxter, San Diego, CA (US); Yuta Fujiwara, Hokkaido (JP)

( * ) Notice: Subject to any disclaimer, the term of this patent is extended or adjusted under 35 U.S.C. 154(b) by 121 days.

(21) Appl. No.: 14/363,974

(22) PCT Filed: Nov. 27, 2012

(86) PCT No.: PCT/US2012/066653
§ 371 (c)(1),
(2) Date: Jun. 9, 2014

(87) PCT Pub. No.: WO2013/082028
PCT Pub. Date: Jun. 6, 2013

(65) Prior Publication Data
US 2015/0011760 A1    Jan. 8, 2015

Related U.S. Application Data

(60) Provisional application No. 61/565,756, filed on Dec. 1, 2011.

(51) Int. Cl.
| | | |
|---|---|---|
| C07C 313/04 | (2006.01) |
| C07F 3/06 | (2006.01) |
| C07D 473/04 | (2006.01) |
| C07B 37/02 | (2006.01) |
| C07B 39/00 | (2006.01) |
| C07D 233/84 | (2006.01) |
| C07D 263/58 | (2006.01) |
| C07D 277/74 | (2006.01) |

(52) U.S. Cl.
CPC .............. *C07D 473/04* (2013.01); *C07B 37/02* (2013.01); *C07B 39/00* (2013.01); *C07C 313/04* (2013.01); *C07D 233/84* (2013.01); *C07D 263/58* (2013.01); *C07D 277/74* (2013.01)

(58) Field of Classification Search
CPC ................................ C07C 313/04; C07F 3/06
USPC .................................................... 556/118, 119
See application file for complete search history.

(56) References Cited

U.S. PATENT DOCUMENTS 4,424,382 A    1/1984   Olah

OTHER PUBLICATIONS

International Search Report for related PCT App. No. PCT/US2012/066653 dated Mar. 29, 2013.
Fujiwara, Yuta et al., "A New Reagent for Direct Difluoromethylation", J. Am. Chem. Soc., vol. 134, pp. 1494-1497 Jan. 9, 2012.
Ji, Yining et al., "Innate C—H trifluoromethylation of heterocycles" Proceedings of the National Academy of Science of the United States of America, vol. 108, No. 35, pp. 14411-14415 Aug. 30, 2011.
Billard, Tierry et al., "A New Route to Thio-and Selenosulfonates from Disulfides and Diselenides. Application to the Synthesis of New Thio- and Selenoesters of Triflic Acid.", J. Org. Chem., vol. 61 pp. 7545-7550 Oct. 18, 1996.

*Primary Examiner* — Golam M M Shameem
(74) *Attorney, Agent, or Firm* — Husch Blackwell, LLP

(57) ABSTRACT

A reagent for carrying out a difluoromethylation reaction of unsaturated compounds and ring-nitrogen-containing aromatic compounds, a zinc difluoro-methanesulfinate, as well as a method for making the reagent and a method for its use are disclosed.

10 Claims, No Drawings

DIFLUOROMETHYLATION OF UNSATURATED COMPOUNDS

CROSS-REFERENCE TO RELATED APPLICATION

This application claims priority from provisional application No. 61/565,756 filed Dec. 1, 2011, whose disclosures are incorporated herein by reference.

GOVERNMENTAL SUPPORT

The present invention was made with governmental support pursuant to grant GM-073949 from the National Institutes of Health/National Institute of General Medical Sciences. The government has certain rights in the invention.

TECHNICAL FIELD

The present invention relates to the preparation of difluoromethylated organic compounds, and more particularly to a reagent, zinc difluoromethanesulfinate, its preparation and use for the preparation of difluoromethylated compounds.

BACKGROUND ART

Difluoromethylated compounds are becoming more common in the pharmaceutical industry. Illustrative examples of such compounds include eflornithine, an ornithine decarboxylase inhibitor used for treating sleeping sickness; pantoprazole, a proton pump inhibitor used for treating stomach erosion and ulceration; afloqualone, a nicotinic antagonist marketed as a mylorelaxant; and fluticasone propionate, that is used against a wide spectrum of inflammatory conditions. See, Hu et al., *Chem. Commun.*, 7465-7478 (2009).

Contrary to their trifluoromethyl relative, difluoromethyl arenes are relatively understudied. The difluoromethyl group is a highly sought after motif for which chemists currently do not have good routes of access.

Currently, the main method used to prepare difluoromethyl arenes is treatment of the corresponding aldehyde with diethylaminosulfur trifluoride (DAST) or $SF_4$. More recently, Amii and coworkers [Fujikawa et al., *Org. Lett.*, 13(20):5560-5563 (2011)] illustrated that a copper-mediated coupling of $CF_2H$ to an iodobenzene could be a possibility.

It was already known that, unlike $CF_3-$, $CF_2H-$ complexes with copper are thermally unstable. Therefore, Amii and co-workers adjusted their strategy and focused on first forming a $-CF_2R$ bond, then converting $CF_2R$ into $CF_2H$. One way to do this was to stabilize the $CF_2$ anion by placing it alpha to a carbonyl. To simplify and enable better control of conditions, they used alpha silyl esters with the general formula $R_3SiCF_2CO_2Et$. The reaction sequence is illustrated below.

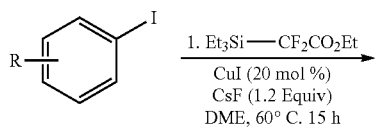

1. $Et_3Si-CF_2CO_2Et$
CuI (20 mol %)
CsF (1.2 Equiv)
DME, 60° C. 15 h

-continued

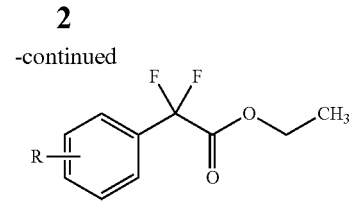

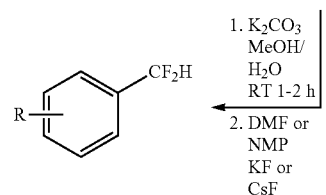

1. $K_2CO_3$ MeOH/$H_2O$ RT 1-2 h
2. DMF or NMP KF or CsF

An earlier-reported synthesis utilized potassium (trifluoromethyl)trimethoxyborane as a new source of $CF_3$ nucleophiles in copper-catalyzed trifluoromethylation reactions. The crystalline salt was reported as being stable on storage, easy to handle, and can be obtained in near-quantitative yields simply by mixing $B(OMe)_3$, $CF_3SiMe_3$, and KF. This trifluoromethylation reagent also permits the conversion of various aryl iodides into the corresponding benzotrifluorides in high yields under mild, base-free conditions in the presence of catalytic quantities of a $Cu^I$/1,10-phenanthroline complex. [Knauber et al., *Chem.-Eur. J.* 17:2689-2697 (2011).]

Although a step forward, the above reaction sequences still need an alternative concept. One of the inventors and coworkers recently published a new method of adding trifluoromethyl free radicals to aryl heterocycles using Langlois reagent: $F_3CSO_2Na$ and t-BuOOH in the absence of added metal catalyst. Yields of trifluoromethylated products were reported to be between about 33 and 90 percent. [Ji et al., *Pro Natl Acad Sci USA*, 108:14411-14415 (2011).]

Attempts to expand that work with a model reactant used in that prior study, caffeine, with $F_2HCSO_2Na$ and t-BuOOH in the absence of added metal catalyst provided no difluoromethylated product. When $F_2HCSO_2Li$ was tried in place of $F_2HCSO_2Na$, the reaction did not go to completion, although some product was formed. Thus, as noted in their "Conclusions and future directions", Hu et al., *Chem. Commun.*, 7465-7478 (2009), noted that both electrophilic and free radical di- and monofluoromethylations are less explored compared to nucleophilic di- and monofluoromethylations, and that transition metal-catalyzed (or mediated) di- and monofluoromethylation have rarely been known.

The comments of Hu et al. notwithstanding, further work led to the preparation of a new reagent that is uniquely able to provide difluoromethylation of unsaturated compounds in high yield. The new reaction route serves as a practical process to prepare the unprecedented difluoromethylating agent zinc difluoromethanesulfinate hydrate.

BRIEF DESCRIPTION OF THE INVENTION

The present invention contemplates difluoromethylation, a reagent for carrying out that reaction as well as a method for making the reagent and for its use. Thus, in one aspect, the invention contemplates a zinc difluoromethanesulfinate, and preferably a zinc difluoromethanesulfinate hydrate as a reagent.

A method of preparing a zinc difluoro-methanesulfinate is another contemplated aspect of the invention. That method comprises the steps of forming an admixture of zinc particles and water in a vessel, preferably a pressure vessel, and the composition cooled to about zero degrees C. $HCF_2SO_2Cl$ is then added, the vessel sealed and permitted to come to ambient room temperature, while the contents therein are admixed until the $HCF_2SO_2Cl$ has reacted. The unreacted zinc powder is separated from the remaining reaction mixture, and the water is removed to provide the desired zinc difluoromethanesulfinate hydrate. The zinc difluoromethanesulfinate hydrate so formed is typically a pearly off-white solid and is typically recovered, but can be reacted directly without recovery.

In another aspect, the invention contemplates the use of a zinc difluoromethanesulfinate reagent to directly difluoromethylate an unsaturated compound that is a heteroaryl or α,β-unsaturated compound, particularly a heteroaryl compound, and more particularly, a heteroaryl compound containing one or more nitrogen atoms in the aromatic ring, and preferably containing one, two or three aromatic rings. Thus, a method of difluoromethylation is contemplated. In accordance with that method, an unsaturated compound as above is reacted using vigorous agitation with an excess of zinc difluoromethanesulfinate hydrate and an excess of tert-butyl hydroperoxide in a water-containing liquid reaction mixture. In some embodiments, an initial temperature below about 10° C. is utilized. The reaction mixture is maintained until the reaction is completed. When initially below ambient room temperature, the reaction mixture is preferably permitted to warm to ambient room temperature during that maintenance time period. The difluoromethylated product so prepared is preferably collected, but can be maintained in the reaction mixture and reacted further, if desired, as where a second difluoromethyl group is added.

The present invention has several benefits and advantages. One benefit is that it provides a reagent that can add a difluoromethyl group to a desired unsaturated compound.

An advantage of the invention is that the difluoromethylation reaction is a direct reaction; i.e., the reaction proceeds without the preparation of an isolated intermediate compound that must be further acted upon to form the difluoromethylated product as in the case of the work of Amii and co-workers discussed above.

Another benefit of the invention is that the zinc difluoromethanesulfinate reacts to difluoromethylate its substrates under mild reaction conditions and in the presence of air.

Another advantage of the invention is that many difluoromethylation reactions proceed with yields in excess of 50%, and some in excess of 80%.

Still further benefits and advantages of the invention will be apparent to the worker of ordinary skill from the disclosure that follows.

DETAILED DESCRIPTION OF THE INVENTION

The present invention contemplates a reagent, a method for making that reagent, as well as a method for using that reagent to prepare difluoromethylated compounds.

Reagent

The reagent is zinc difluoromethanesulfinate hydrate. The hydrate can exist in different levels of hydration in which the zinc difluoromethanesulfinate is hydrated with one to about four waters per zinc difluoromethanesulfinate molecule. The trihydrate is particularly preferred. The chemical formula for zinc difluoromethanesulfinate hydrate is $Zn(O_2SCHF_2)_2 \cdot xH_2O$, where x is 1 to about 4.

Reagent Preparation

A contemplated method for preparing zinc difluoromethanesulfinate hydrate involves the steps of forming an admixture of zinc particles and water in a vessel that is preferably a pressure vessel and the admixture is cooled to about zero degrees C. The zinc particles used can be as fine as zinc dust that is typically less than about 10 μm (about 1250 to about 2500 mesh) in largest dimension, to zinc powder that typically passes through a 100 sieve screen, to zinc shot that has a largest dimension of about 1-2 mm passes through a Tyler sieve mesh size of about 10 to about 18 mesh).

The zinc is present in an excess over the amount of difluoromethylsulfonyl chloride to be used. The molar ratio of zinc to difluoromethylsulfonyl chloride is typically about 2:1 to about 10:1, and preferably about 5:1 to about 8:1.

Difluoromethylsulfonyl chloride ($HCF_2SO_2Cl$) is then added, the vessel sealed and permitted to come to ambient room temperature, while the contents therein are admixed until the $HCF_2SO_2Cl$ has reacted. The reaction vessel need not be sealed, so long as adequate cooling is maintained to prevent escape of the difluoromethylsulfonyl chloride. The use of a sealed pressure vessel is preferred.

The unreacted zinc powder is separated from the remaining reaction mixture, and the water is removed to provide the desired zinc difluoromethanesulfinate hydrate. The zinc difluoromethanesulfinate hydrate so formed is typically a pearly off-white solid and is typically recovered, but can be reacted directly without recovery.

Several other metal ions have been examined as the cation in place of zinc, but zinc difluoromethanesulfinate is the only metal salt that was capable of forming difluoromethyl compounds in high yields. The preparation procedures used for the preparation of the zinc salt was followed with copper, iron and indium to form the corresponding difluoromethanesulfinates. No difluoromethylated product was formed using those reagents. Preparation with magnesium provided a poor yield (36%) of magnesium difluoromethanesulfinate trihydrate. As noted before, sodium difluoromethanesulfinate was prepared and formed no product when reacted with caffeine and t-butyl hydroperoxide as described herein. Similarly, the corresponding lithium salt was prepared and performed poorly in that reaction.

It is noted that even though the magnesium salt was obtained, the yield of that reagent was significantly lower than that of the zinc salt. Similarly, the reactivity of the magnesium salt with caffeine did not result in complete conversion to the difluoromethylated product as occurred with the zinc salt (Examples 3 and 4). Additionally, the magnesium salt was noticeably more hygroscopic than the zinc salt.

Hydration levels of the zinc salt can differ, with one to about four water molecules per zinc difluoromethanesulfinate molecule being present. Three water molecules per molecule of zinc difluoromethanesulfinate is a typical amount and is preferred.

A non-hydrated salt can be prepared from a hydrate by dissolution or trituration of the hydrate in a dry, water-sorbing solvent such as absolute ethanol or by boiling of the solid hydrate in a solvent such as benzene or toluene and removing the water by azeotropic distillation.

Difluorormethylation Method

Zinc difluoromethanesulfinate is utilized in the preparation of a difluoromethylated unsaturated substrate compound that is other than a hydrocarbon compound. This difluoromethylation reaction is a direct reaction; i.e., the reaction proceeds without the preparation of an isolated intermediate compound that must be further acted upon to form the difluoromethylated heteroaryl or α,β-unsaturated compound reaction product as was the case in the work of most others. Thus, Chen et al., *J Chem Soc, Chem Commun*, 737-738 (1994), reported the preparation of difluoroiodomethane, a gas at ambient temperatures, that reacted with alkenes and alkynes in the presence of sodium dithionite to directly form difluoromethylated adducts via carbene insertion.

Here, a zinc difluoromethanesulfinate reagent is used to difluoromethylate an unsaturated substrate compound that is a heteroaryl, or an α,β-unsaturated compound. A heteroaryl compound, and more particularly, a heteroaryl compound containing one or more nitrogen atoms in the aromatic ring system is particularly preferred. The heteroaryl compound can contain 1 to 5 heteroatoms in the ring system that is difluoromethylated, and typically contains 1 to 3.

An unsaturated substrate compound as above described is reacted using vigorous agitation with an excess of zinc difluoromethanesulfinate and an excess of tert-butyl hydroperoxide in an aqueous liquid solvent reaction mixture. The difluoro-methylation likely occurs at the interface of the biphasic mixture by generation of a difluoromethyl radical ($HCF_2\cdot$) and insertion of that radical into the substrate, followed by bond and/or hydrogen rearrangement. The reaction mixture is preferably maintained with that agitation until the reaction is completed. The difluoromethylated product so prepared is preferably collected, but can be maintained in the reaction mixture and reacted further, if desired.

A contemplated difluoromethylation reaction can be carried out entirely at or near ambient room temperature; i.e., in the absence of externally-supplied heating or cooling of the reaction mixture. In some embodiments, it is preferred that the unsaturated substrate compound and the excess of zinc difluoromethanesulfinate be agitated in an aqueous solvent at an initial temperature below about 10° C. When such a chilled temperature is utilized, the reaction mixture is preferably permitted to warm to ambient room temperature during that maintenance time period.

In preferred practice, the unsaturated substrate compound and a zinc difluoromethanesulfinate such as the trihydrate are first admixed in the aqueous solvent medium and the excess tert-butyl hydroperoxide is added slowly to that agitated, first-formed admixture (first reaction mixture). If the addition of tert-butyl hydroperoxide is performed too rapidly, the resulting exotherm can result in reduced yield and selectivity. This is especially important on larger scales, where a syringe pump may be used to meter in tert-butyl hydroperoxide.

Total reaction times are typically about 2 to about 24 hours, with the more reactive reactions being completed in about 3 to about 6 hours. If the unsaturated substrate compound is not consumed within 24 hours, another addition of zinc difluoromethanesulfinate and tert-butyl hydroperoxide is made using added amounts that are proportional to the unreacted substrate.

Where a heteroaryl compound is the unsaturated substrate and it is desired to add two difluoromethyl substituents per substrate molecule, another excess of zinc difluoromethanesulfinate is admixed with the reaction mixture formed after the first difluoromethylation, and the reaction mixture so formed is agitated. An excess of tert-butyl hydroperoxide is again admixed as discussed before. Also as previously discussed, the reaction can be carried out in the absence of externally-supplied heating or cooling, or admixture of excess of zinc difluoromethanesulfinate and once-difluoromethylated substrate can be chilled to a temperature below about 10° C. Of course, if desired, the mono-difluoromethylated product can be recovered prior to undergoing the second difluoromethylation reaction.

The molar ratio of zinc difluoromethanesulfinate hydrate to unsaturated substrate is about 2:1 to about 5:1, and preferably about 3:1 to about 4:1. Greater ratios can be used, but they tend to be wasteful of the reagents.

The molar ratio of tert-butyl hydroperoxide to unsaturated substrate is about 3:1 to about 7:1, and preferably about 4:1 to about 6:1. Again, greater ratios can be used, but they tend to be wasteful of the reagents.

Illustrative unsaturated substrates include the following heteroaryl compound ring systems that preferably contain up to three aromatic rings and more preferably contain one or two aromatic rings: pyridine, pyrimidine, imidazole, 7H-purine, purinedione, isoquinoline, quinoline, 1,3,4-1,2,4- or 1,2,5-thiadiazole, quinoxaline, pyridazine, pyrazolo[1,5-a]pyridine, 1H-pyrazole, 1H-pyrrole, thiophene, 1,2,3-triazole, 1,2,4-triazole, indazole, indoxazine, benzoxazole, anthranil, isoxazole, oxazole, thiazole, isothiazole, isothiazole, 1,2,3-oxadiazole, 1,3,4-oxadiazole, pyridazine, 1,3,5-1,2,4- or 1,2,3-triazine, indole, cinnoline, quinazoline, and naphthyridine. Illustrative additional α,β-unsaturated substrate compounds include chromone, coumarin and 2-cyclohexene-1-one.

The aqueous solvent can contain only water. Preferably, however, the aqueous solvent is a mixture that contains about 40 percent by volume dichloromethane (DCM). If an unsaturated substrate compound fails to react or gives unfavorable selectivity, DMSO can be substituted for DCM as a cosolvent, as it causes substrate-dependent changes in reactivity. For more polar substrates, ethyl acetate (EtOAc) can be used in place of DCM for extractive workup. Additional useful organic solvents include chloroform, 1,2-dichloroethane, acetone, methyl ethyl ketone (MEK), dimethylformamide (DMF), dimethylacetamide (DMA), N-methylpyrrolidone (NMP), α, α, α-trifluorotoluene and the like. The organic cosolvent can be water-miscible, or have a solubility in water of at least about one percent, e.g., DCM=1.3%, chloroform=0.8%, 1,2-dichloroethane=0.8%.

When reacted in a water-dichloromethane solvent, the difluoromethylation of a 4-substituted pyridine produced the 2-position difluoromethyl group almost exclusively, whereas when DMSO replaced dichloromethane, the reaction products exhibited a 3:2 ratio for the 3-position relative to the 2-position substitution. Additions to α,β-unsaturated substrate compounds occur in a 1,4-manner, whereas additions to oxy-vinylic compounds occur across the ethylenic bond in an anti-Markovnikoff manner.

Materials and Methods

General Information

All reactions were carried out under an air atmosphere. Reagents were purchased at the highest commercial quality and used without further purification, unless otherwise stated. All reactions were carried out with dry solvents unless otherwise stated. Dry dichloromethane (DCM), tetrahydrofuran (THF), N,N-dimethylformamide (DMF), and triethylamine ($NEt_3$), were obtained by passing the previously degassed solvents through activated alumina columns.

Yields refer to chromatographically and spectroscopically ($^{1}H-$, $^{13}C-$, $^{19}F-NMR$) homogeneous material, unless otherwise stated. Reactions were monitored by thin layer chromatography (TLC) carried out on 0.25 mm E. Merck silica plates (60E-254), using UV light as the visualizing agent and $KMnO_4$ as a developing agent. Alternatively, reactions were monitored by HPLC-MS on a reverse phase column, using acetonitrile/water/0.1% formic acid as the mobile phase. Flash silica gel chromatography was performed using E. Merck silica gel (60, particle size 0.043-0.063 mm). Preparative HPLC was performed using a Phenomenex Gemini® C18 110 Å AXIA 5 μm column with dimension 30 or 50×100 mm, unless otherwise noted.

NMR spectra were recorded on Bruker DRX-600, DRX-500, AMX-400, and Varian INOVA-399 instruments and were calibrated using residual undeuterated solvent as an internal reference (CHCl$_3$ @ 7.26 ppm $^1$H-NMR, 77.16 ppm $^{13}$C-NMR; CD$_3$OD @ 3.31 ppm $^1$H-NMR, 49.0 ppm $^{13}$C-NMR; CD$_3$CN 1.94 ppm $^1$H-NMR, 1.32 ppm $^{13}$C-NMR). $^{19}$F-NMR spectra were recorded referenced to trichlorofluoromethane. The following abbreviations were used to explain multiplicities: s=singlet, d=doublet, t=triplet, q=quartet, m=multiplet, br=broad.

Gas chromatography was performed on an Agilent Technologies 7890A instrument using a 30 meter DB-5 column with an internal diameter of 0.250 millimeters; reaction species were calibrated against tetradecane as an internal standard. High resolution mass spectra (HRMS) were recorded on an Agilent LC/MSD TOF mass spectrometer by electrospray ionization time of flight reflectron experiments. IR experiments were recorded on a Perkin Elmer Spectrum BX FTIR spectrometer. Preparative HPLC was performed using a Waters Atlantis dC18 OBD 10 μm column with dimension 30×250 mm, unless otherwise noted. Melting points were recorded on a Fisher-Johns 12-144 melting point apparatus and are uncorrected.

Example 1

Preparation of Zn(SO$_2$CF$_2$H)$_2$.xH$_2$O

Difluoromethylsulfonyl chloride (HCF$_2$SO$_2$Cl) was purchased from Enamine LLC, Monmouth Junction, NJ. To a pressure vessel equipped with a stir bar, zinc (Zn) dust (4.11 g, 62.85 mmol) was added followed by H$_2$O (5.0 mL). The reaction vessel was then capped and cooled in an ice bath. HCF$_2$SO$_2$Cl (798 μL, 9.00 mmol) was then added via syringe open to air. The reaction vessel was sealed with a threaded Teflon® cap and the reaction mixture was then removed from the ice bath and permitted to stir at room temperature for 2 hours. The excess Zn was removed via filtration through a sintered glass filter, washed with EtOAc, the liquid concentrated. Residual water was removed azeotropically with toluene (25 mL, 3 times) at 45° C. resulting in a pearly white powder. The product was then dried under vacuum for three hours (2.01 g, 64% based on Zn(SO$_2$CF$_2$H)$_2$.xH$_2$O where x=3). $^1$H-NMR (400 MHz, DMSO-d$_6$): δ 5.30 (t, J=56.0 Hz, $^1$H); $^{13}$C-NMR (150 MHz, CDCl$_3$) δ 123.5 ppm (t, J=282.0 Hz); $^{19}$F-NMR (376 MHz, DMSO-d$_6$): δ −125.9 ppm (referenced to trichlorofluoromethane).

Example 2

Difluoromethylation of Caffeine (2)

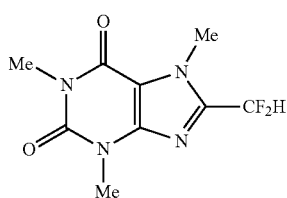

2

To a solution of caffeine (9.7 mg, 0.05 mmol, 1.0 equiv) and Zn(SO$_2$CF$_2$H)$_2$.xH$_2$O (44.3 mg, 0.15 mmol, 3.0 equiv as anhydride) in dichloromethane (100 μL) and water (40 μL) at zero ° C. was slowly added tert-butyl hydroperoxide (70% solution in water, 34 μL, 0.25 mmol, 5.0 equiv) open to air with vigorous stirring. The reaction vial was then capped and removed from the ice bath and permitted to warm to room temperature. The reaction was complete after 3 hours by TLC analysis.

The reaction mixture was partitioned between dichloromethane (DCM; 2.0 mL) and saturated sodium bicarbonate (2.0 mL). The organic layer was separated, and the aqueous layer was extracted with dichloromethane (3×2.0 mL). The combined organic layer was dried over Na$_2$SO$_4$. Removal of the solvent gave difluoromethylated-caffeine. The product was redissolved in DCM and loaded onto a column of silica gel eluting with 30% EtOAc/70% hexanes. Following the removal of solvent, a white solid was obtained in 79% yield. $^1$H NMR (400 MHz, CDCl$_3$): δ 6.74 (t, J=52 Hz, 1H), 4.16 (s, 3H), 3.57 (s, 3H), 3.41 (s, 3H); $^{19}$F NMR (376 MHz, CDCl$_3$): δ −115.2 ppm (referenced to trichlorofluoromethane).

Example 3

Preparation of M (SO$_2$CF$_2$H)$_2$.xH$_2$O

To a vial equipped with a stir bar, Mg powder (170 mg, 6.99 mmol) was added followed by H$_2$O (0.56 mL). The reaction vial was then capped, wrapped in aluminum foil and cooled in an ice bath. HCF$_2$SO$_2$Cl (89 μL, 1.00 mmol) was then added via syringe open to air. The reaction vial was capped and the reaction mixture was then removed from the ice bath and permitted to stir at room temperature for 21 hours. The excess Mg was removed via filtration through a filter paper, washed with EtOAc, and the liquid was concentrated. Residual water was removed azeotropically with benzene (10 mL, 3 times) at 40° C. resulting in a pearly white powder. The product was then dried under vacuum for three hours (110 mg, 36% based on Mg(SO$_2$CF$_2$H)$_2$.xH$_2$O where x=3). $^1$H NMR (400 MHz, DMSO-d$_6$): δ 4.98 (t, J=56.2 Hz, 1H); $^{19}$F NMR (376 MHz, DMSO-d$_6$): δ −125.6 ppm (referenced to trichlorofluoromethane).

Example 4

Difluoromethylation of Caffeine

To a solution of caffeine (9.7 mg, 0.05 mmol, 1.0 equiv) and Mg(SO$_2$CF$_2$H)$_2$.xH$_2$O (38.2 mg, 0.15 mmol, 3.0 equiv as anhydride) in dichloromethane (100 μL) and water (40 μL) at 0° C. was slowly added tert-butyl hydroperoxide (70% solution in water, 34 μL, 0.25 mmol, 5.0 equiv) open to air with vigorous stirring. The reaction vial was then capped and removed from the ice bath and allowed to warm to room temperature. Although complete conversion of the starting material to the desired product was not observed, the reaction was stopped after six hours. (No further progression of the reaction was observed by TLC analysis after three hours.)

The reaction mixture was partitioned between dichloromethane (2.0 mL) and saturated sodium bicarbonate (2.0 mL). The organic layer was separated, and the aqueous layer was extracted with dichloromethane (3×2.0 mL). The combined organic layer was dried over Na$_2$SO$_4$. Removal of the solvent gave the crude difluoromethylated-caffeine (2) as a white powder (5:1 product:starting material). $^1$H NMR (400

MHz, CDCl₃): δ 6.74 (t, J=52 Hz, 1H), 4.15 (s, 3H), 3.58 (s, 3H), 3.41 (s, 3H); ¹⁹F NMR (376 MHz, CDCl₃): δ −115.2 ppm (referenced to trichlorofluoromethane).

Example 5

Preparation of Other Difluoromethylsulfinate Reagents

A similar procedure was used to try to obtain the lithium, sodium, potassium, cesium, copper, cobalt, iron and indium salts. However, except for lithium, no reaction occurred in each of these cases (only starting material was detected when the reactions were monitored by ¹⁹F NMR). Attempted difluoromethylation of caffeine with the lithium salt resulted in a yield of about 5% after five hours.

Example 6

Preparation of Difluoromethylated Unsaturated Compounds

The following difluoromethylated unsaturated compounds were prepared using Zn(SO₂CF₂H)₂·xH₂O and following the procedures of Example 2 except the preparation of difluoromethylated caffeine was scaled-up from 0.05 mmol to 0.25 mmol. One reaction was carried out in DMSO.

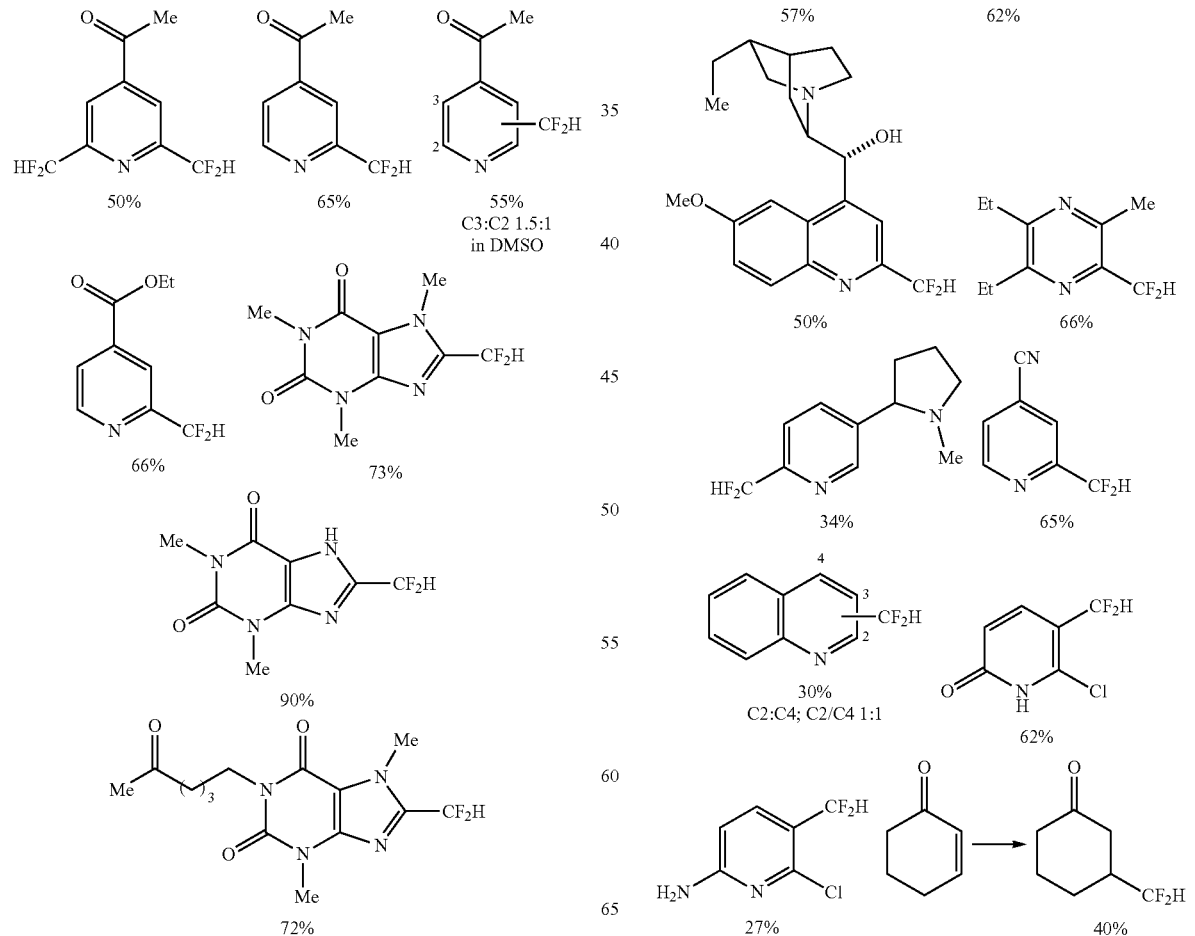

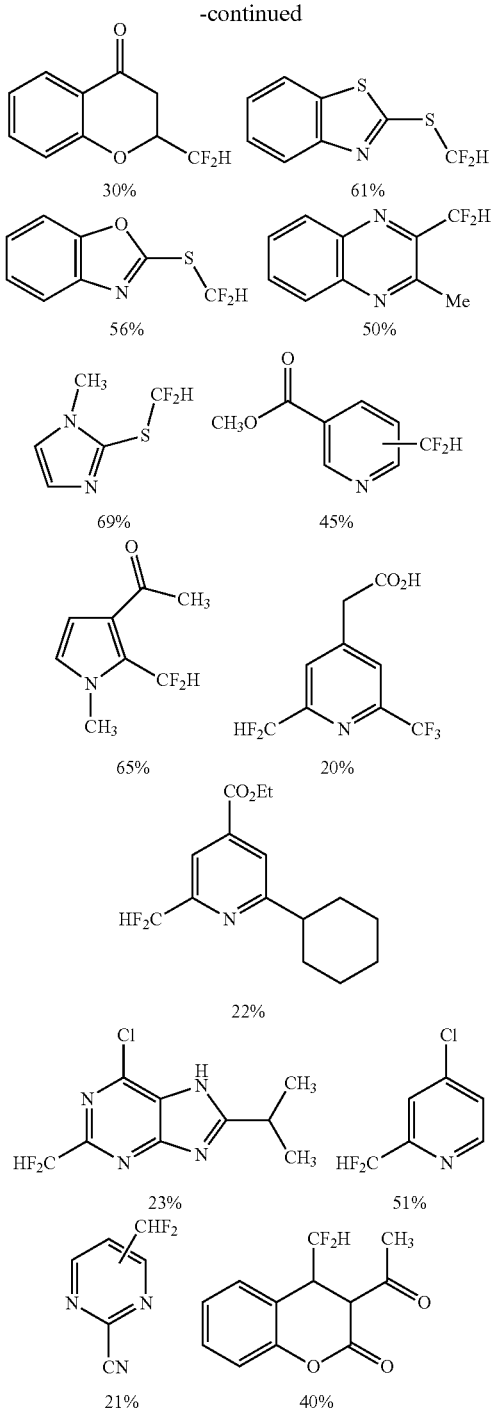

Difluoromethylation of Heterocycles Standard Procedures: Procedure A:

To a solution of heterocycle (0.25 mmol, 1.0 equiv) and zinc difluoromethanesulfinate (DFMS) (200 mg, 0.50 mmol, 2.7 equiv 'calculated as anhydrous') in dichloromethane (1.0 mL) and water (0.4 mL) at room temperature was added trifluoroacetic acid (20 µL, 0.25 mmol, 1.0 equiv) followed by slow addition of tert-butyl hydroperoxide (70% solution in water, 0.17 mL, 1.25 mmol, 5.0 equiv) with vigorous stirring. The reaction was monitored by thin layer chromatography until completion. For substrates that do not react to completion in 24 hours, a second addition of DFMS (2.7 equiv) and tert-butyl hydroperoxide (5.0 equiv) may be added to drive the reaction further. Upon consumption of starting material, the reaction was partitioned between dichloromethane (2.0 mL) and saturated sodium bicarbonate (2.0 mL). The organic layer was separated, and the aqueous layer was extracted with dichloromethane (3×2.0 mL). The combined organic layers were dried with sodium sulfate, concentrated and purified by column chromatography on silica gel.

Procedure B:

To a solution of heterocycle (0.25 mmol, 1.0 equiv) and zinc difluoromethanesulfinate (DFMS) (173 mg, 0.50 mmol, 2.0 equiv 'calculated as anhydrous') in dichloromethane (1.0 mL) and water (0.4 mL) at room temperature was added trifluoroacetic acid (20 µL, 0.25 mmol, 1.0 equiv) followed by slow addition of tert-butyl hydroperoxide (70% solution in water, 0.1 mL, 0.75 mmol, 3.0 equiv) with vigorous stirring. The reaction was monitored by thin layer chromatography until completion. For substrates which do not go to completion in 24 hours, a second addition of DFMS (2.0 equiv) and tert-butyl hydroperoxide (3.0 equiv) may be added to drive the reaction further. Upon consumption of starting material, the reaction was partitioned between dichloromethane (2.0 mL) and saturated sodium bicarbonate (2.0 mL). The organic layer was separated, and the aqueous layer was extracted with dichloromethane (3×2.0 mL). The organic layers were dried with sodium sulfate, concentrated and purified by column chromatography on silica gel.

If substrates are less reactive, α, α, α-trifluorotoluene can be substituted for DCM, as it causes improved reactivity for some cases. For water-soluble starting materials, a purely aqueous reaction (1.0 mL of water) can be run and in some cases, it was also found to display improved reactivity. In lieu of a workup, these reactions can be concentrated and the product purified directly. If the addition of tert-butyl hydroperoxide is performed too rapidly, the resulting exotherm can result in reduced yield and selectivity. This is especially important on larger scales (see gram scale procedure: substrate 2), where a syringe pump can be used to meter in tert-butyl hydroperoxide.

It is noted that trifluoroacetic acid (TFA) is not required in either of the above procedures. It was also found that TFA showed improved rate and conversion for selected nitrogen heteroarene substrates, but was not essential to achieve the desired reactivity for most cases. When present, TFA is typically used at about 0.25 to about 2 equivalents per equivalent of nitrogen heteroarene, and more preferably at about 0.5 to about 1.5 equivalents relative to the nitrogen heteroarene.

Zinc Difluoromethanesulfinate (DFMS, 3).

To a pressure vessel equipped with a stir bar, Zn dust (61.74 g, 94.42 mmol) was added followed by H2O (75 mL). The reaction vessel was then capped, wrapped in aluminum foil and cooled in an ice bath to 0° C. Difluoromethanesulfonyl chloride (12 mL, 135.2 mmol) was then added via syringe open to air over five minutes. The reaction vessel was sealed with a threaded Teflon® cap and the reaction mixture was then removed from the ice bath and permitted to stir at room temperature for 2 hours. The excess Zn was removed via filtration through a sintered glass filter, washed with EtOAc (100 mL×5) then concentrated under reduced pressure. Residual water was removed azeotropically with toluene (100 mL×3) at 45° C., the resulting pearly white powder was further dried under vacuum for an additional 3 hours (35 g, 85% based on anhydrous). The product probably also contained ZnCl2 which could not be separated from the DFMS. As there are two equivalents of sulfonyl chloride for each Zn, the theoretical yield of the DFMS could only be as high as 67.6 mmol (20 g). However, because the product likely contained water and $ZnCl_2$, the yield could not be accurately determined. $^1$H-NMR (400 MHz, DMSO-d6) δ 5.30 (t, J HF=56.0 Hz, 1H); $^{13}$C-NMR (150 MHz, DMSO-d6) δ 123.5 (t, J CF=282.0 Hz); $^{19}$F-NMR (376 MHz, DMSO-d6) δ −125.9; IR (neat) ν=1618, 1097, 950 cm$^{-1}$.

Ethyl 2-(difluoromethyl)isonicotinate

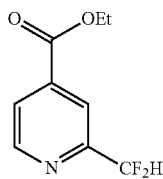

Standard Procedure A was followed with a reaction time of 1 hour (no second addition of reagents needed) to provide 5 in 66% yield as a colorless oil; Rf=0.4 (25% dichloromethane/hexanes); $^1$H-NMR (400 MHz, CDCl$_3$) δ 8.80 (dd, J=5.0, 0.7 Hz, 1H), 8.18 (s, 1H), 7.97 (ddd, J=5.0, 1.7, 0.9 Hz, 1H), 6.69 (t, JHF=55.0 Hz, 1H), 4.44 (q, J=7.1 Hz, 2H), 1.42 (t, J=7.1 Hz, 3H); $^{13}$C-NMR (150 MHz, CDCl$_3$) δ 164.4, 154.0 (t, JCF=25.5 Hz), 150.5, 139.4, 124.8, 119.7, 113.6 (t, JCF=238.5 Hz), 62.4, 14.3; $^{19}$F-NMR (376 MHz, CDCl$_3$) δ 116.3; IR (neat) ν=2986, 1727, 1371, 1292, 1211, 1117, 1040, 762 cm$^{-1}$; HRMS (ESI-TOF) calc'd for $C_9H_{10}F_2NO_2$ [M+H] 202.0674. found 202.0665.

1-(2-(difluoromethyl)pyridin-4-yl)ethanone (6-C2) and 1-(3-(difluoromethyl)pyridin-4-yl)ethanone (6-C3)

C-2 Selective

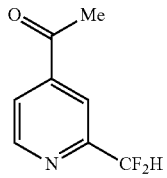

Standard Procedure A was followed with a reaction time of 17 hours (no second addition of reagents needed) to provide 6 in 65% yield (C2:C3>10:1).
C-3 Selective Procedure:

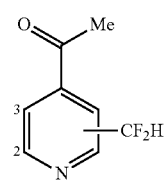

Standard Procedure A was followed (DMSO used instead of dichloromethane) with a reaction time of 12 hours followed by a second addition of DFMS and tert-butyl hydroperoxide to provide 6 in 55% yield (C2:C3 1:1.5).

Data for 6-C2: colorless oil; Rf=0.30 (30% EtOAc/Hexanes); $^1$H-NMR (400 MHz, CDCl$_3$) δ 8.85 (d, J=5.0 Hz, 1H), 8.06 (s, 1H), 7.87-7.84 (m, 1H), 6.71 (t, JHF=55.3 Hz, 1H), 2.67 (s, 3H). $^{13}$C-NMR (150 MHz, CDCl$_3$) δ 196.4, 154.4 (t, JCF=25.5 Hz), 150.9, 144.3, 123.1, 118.1, 113.6 (t, JCF=238.5 Hz), 26.9; $^{19}$F-NMR (376 MHz, CDCl$_3$) δ −116.3; IR (neat) ν=2923, 1699, 1372, 1265, 1201, 1037, 849, 767 cm$^{-1}$; HRMS (ESI-TOF) calc'd for $C_8H_8F_2NO$ [M+H] 172.0568. found 172.0575.

Data for 6-C3: colorless oil; Rf=0.28 (30% EtOAc/Hexanes); $^1$H-NMR (400 MHz, CDCl$_3$) δ 9.04 (s, 1H), 8.90 (d, J=4.6 Hz, 1H), 7.61-7.52 (m, 1H), 7.29 (t, JHF=55.0 Hz, 1H), 2.63 (s, 3H); $^{13}$C-NMR (151 MHz, CDCl$_3$) δ 199.6, 153.0 (t, JCF=2.0 Hz), 148.5 (t, JCF=9.0 Hz), 143.2 (t, JCF=4.6 Hz), 127.1 (t, JCF=22.4 Hz), 121.6, 111.8 (t, JCF=239.0 Hz), 29.0; $^{19}$F-NMR (376 MHz, CDCl$_3$) δ −115.0; IR (neat) ν=2923, 1699, 1372, 1265, 1201, 1037, 849, 767 cm$^{-1}$. HRMS (ESI-TOF) calc'd for $C_8H_8F_2NO$ [M+H] 172.0568. found 172.0577.

methyl 2-(difluoromethyl)nicotinate (7-C2), methyl 4-(difluoromethyl)nicotinate (7-C4), and methyl 6-(difluoromethyl) nicotinate (7-C6)

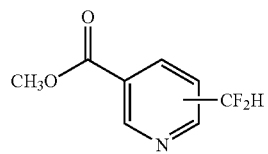

Standard Procedure B was followed with a reaction time of 24 hours (no second addition of reagents needed) to provide 7 in 45% yield (C2:C4:C6 1.5:1.5:2).

Data for 7-C2: clear oil; Rf=0.25 (25% EtOAc/hexanes); $^1$H-NMR (400 MHz, DMSO-d6) δ 8.89 (dd, J=4.8, 1.6 Hz, 1H), 8.38-8.25 (m, 1H), 7.80-7.67 (m, 1H), 7.42 (t, JHF=54.0 Hz, 1H), 3.90 (s, 3H); $^{13}$C-NMR (175 MHz, CDCl$_3$) δ 165.3, 152.6, 152.1 (t, JCF=22.0 Hz), 139.0, 125.7 (t, JCF=3.0 Hz), 125.2, 110.6 (t, JCF=240.0 Hz), 53.2; $^{19}$F-NMR (376 MHz, DMSO-d6) δ −116.9; IR (neat) ν=3442, 3008, 2958, 2848, 2253, 2088, 1984, 1955, 1728, 1588, 1435, 1377, 1301, 1285, 1272, 1240, 1203, 1145, 1111, 1057, 960, 907, 872, 827, 783 cm$^{-1}$; HRMS (ESI-TOF) calc'd for $C_8H_8F_2NO_2$ [M+H] 188.0518. found 188.0520.

Data for 7-C4: clear oil; Rf=0.25 (25% EtOAc/hexanes); $^1$H-NMR (400 MHz, DMSO-d6) δ 9.14 (d, J=0.9 Hz, 1H), 8.98 (d, J=5.1 Hz, 1H), 7.79 (dt, J=5.1, 0.7 Hz, 1H), 7.54 (t, JHF=54.3 Hz, 1H), 3.92 (s, 3H); $^{13}$C-NMR (175 MHz, CDCl$_3$) δ 165.1, 154.2, 152.1, 143.2 (t, JCF=24.6 Hz), 123.6, 119.9 (t, JCF=8.8 Hz), 110.7 (t, JCF=240.0 Hz), 53.02; $^{19}$F-NMR (376 MHz, DMSO-d6) δ −116.1; IR (neat) ν=3035, 2958, 2847, 2253, 2126, 2026, 1928, 1729, 1593, 1572, 1438, 1408, 1372, 1301, 1288, 1236, 1213, 1175, 1122, 1086, 1047, 962, 907, 841, 828, 784 cm$^{-1}$;

Data for 7-C6: clear oil; Rf=0.50 (25% EtOAc/hexanes); $^1$H-NMR (400 MHz, DMSO-d6) δ 9.17 (dd, J=1.9, 0.9 Hz, 1H), 8.49 (dd, J=8.1, 2.1 Hz, 1H), 7.87 (d, J=8.1 Hz, 1H), 7.07 (t, JHF=54.5 Hz, 1H), 3.92 (s, 3H); $^{13}$C-NMR (150 MHz, CDCl$_3$) δ 165.1, 156.3 (t, JCF=22.5 Hz), 150.7, 138.7, 127.7, 119.9 (t, JCF=1.5 Hz), 113.5 (t, JCF=205.5 Hz), 52.9;

$^{19}$F-NMR (376 MHz, DMSO-d6) δ −116.8; IR (neat) ν=3442, 3053, 3006, 2958, 2851, 2256, 2162, 2081, 1972, 1901, 1726, 1601, 1580, 1487, 1438, 1374, 1288, 1221, 1194, 1121, 1090, 1049, 1025, 952, 907, 885, 855, 821, 776, 731 cm$^{-1}$.

methyl 2-(difluoromethyl)-5-methoxynicotinate (8-C2), methyl 4-(difluoromethyl)-5-methoxynicotinate (8-C4), methyl 6-(difluoromethyl)-5-methoxynicotinate (8-C6)

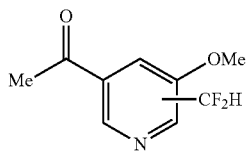

8

Standard Procedure A was followed with a reaction time of 24 hours (no second addition of reagents needed) to provide 8 in 79% yield (C2:C4:C6 1:1:2). Data for 8-C2: yellow solid; m.p.: 82-84° C.; Rf=0.65 (60% EtOAc/hexanes); $^1$H-NMR (400 MHz, CDCl$_3$) δ 7.74 (d, J=2.3 Hz, 1H), 7.32 (d, J=2.4 Hz, 1H), 6.70 (t, JHF=55.0 Hz, 1H), 4.01 (s, 3H), 3.97 (s, 3H); $^{13}$C-NMR (150 MHz, CDCl$_3$) δ 167.9, 165.2, 155.0 (t, JCF=26.0 Hz), 113.6 (t, JCF=240.0 Hz), 113.3, 109.4, 56.2, 53.4; $^{19}$F-NMR (376 MHz, CDCl$_3$) δ −115.6; IR (neat) ν=2923, 2854, 1722, 1594, 1378, 1028 cm$^{-1}$; HRMS (ESI-TOF) calc'd for C$_9$H$_{10}$F$_2$NO$_3$ [M+H] 218.0623. found 218.0624.

Data for 8-C4: yellow wax; Rf=0.50 (60% EtOAc/hexanes); $^1$H-NMR (400 MHz, CDCl$_3$) δ 8.76 (s, 1H), 7.74 (s, 1H), 6.94 (t, JHF=52.0 Hz, 1H), 4.03 (s, 3H), 4.02 (s, 3H); $^{13}$C-NMR (150 MHz, CDCl$_3$) δ 165.3, 164.5, 151.9, 148.0, 121.5 (t, JCF=23.0 Hz), 110.7 (t, JCF=234.0 Hz), 108.2, 56.5, 53.4; $^{19}$F-NMR (376 MHz, CDCl$_3$) δ −117.9; IR (neat) ν=2923, 2854, 1722, 1594, 1378, 1028 cm$^{-1}$;

Data for 8-C6: yellow wax; Rf=0.4 (60% EtOAc/hexanes); $^1$H-NMR (400 MHz, CDCl$_3$) δ 8.59 (d, J=4.0 Hz, 1H), 7.21 (t, JHF=54.0 Hz, 1H), 7.00 (d, J=4.0 Hz, 1H), 3.98 (s, 3H), 3.97 (s, 3H); $^{13}$C-NMR (150 MHz, CDCl$_3$) δ 166.2, 165.0, 153.0, 149.8, 118.0 (t, JCF=23.0 Hz), 110.9 (t, JCF=237.0 Hz), 108.7, 56.4, 53.4; $^{19}$F-NMR (376 MHz, CDCl$_3$) δ −115.9; IR (neat) ν=2923, 2854, 1722, 1594, 1378, 1028 cm$^{-1}$; HRMS (ESITOF) calc'd for C$_9$H$_{10}$F$_2$NO$_3$ [M+H] 218.0623. found 218.0624.

1-(5-bromo-2-(difluoromethyl)pyridin-3-yl)ethanone (9-C2), 1-(5-bromo-4-(difluoromethyl)pyridin-3-yl)ethanone (9-C4), and 1-(5-bromo-6-(difluoromethyl)pyridin-3-yl)ethanone (9-C6)

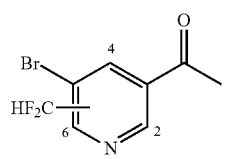

9

Standard Procedure B was followed with a reaction time of 17 hours (no second addition of reagents needed) to provide 9 in 60% yield (C2:C4:C6 3:1:2).

Data for 9-C2: yellow oil; Rf=0.32 (100% dichloromethane); $^1$H-NMR (400 MHz, CDCl$_3$) δ 8.90 (d, J=1.1 Hz, (1H), 8.62 (s, 1H), 7.04 (t, JHF=53.4 Hz, 1H), 2.63 (s, 3H); $^{13}$C-NMR (150 MHz, CDCl$_3$) δ 199.4, 154.7, 147.0, 137.2 (t, JCF=24.0 Hz), 136.5, 120.1, 112.7 (t, JCF=242.4 Hz), 31.6 (t, JCF=2.9 Hz); $^{19}$F-NMR (376 MHz, CDCl$_3$) 5-114.3; IR (neat) ν=3051, 2924, 1692, 1582, 1398, 1355, 1286, 1251, 1192, 1102, 1035, 937, 921, 875, 795, 732 cm$^{-1}$; HRMS (ESI-TOF) calc'd for C$_{11}$H$_8$F$_4$N [M+H] 249.9674. found 249.9684.

Data for 9-C4: yellow oil; Rf=0.50 (100% dichloromethane); $^1$H-NMR (400 MHz, CDCl$_3$) δ 8.85 (d, J=2.2 Hz, 1H), 8.15-8.07 (m, 1H), 7.04 (t, JHF=54.4 Hz, 1H), 2.65 (s, 3H); $^{13}$C-NMR (150 MHz, CDCl$_3$) δ 196.2, 152.6, 148.5 (t, JCF=24.0 Hz), 139.2, 135.0, 122.7, 111.8 (t, JCF=240.0 Hz), 29.8; $^{19}$F-NMR (376 MHz, CDCl$_3$) δ −116.5; IR (neat) ν=3051, 2924, 1692, 1582, 1398, 1355, 1286, 1251, 1192, 1102, 1035, 937, 921, 875, 795, 732 cm$^{-1}$;

Data for 9-C6: white solid; Rf=0.42 (100% dichoromethane); m.p.: 28-30° C. $^1$H-NMR (400 MHz, CDCl$_3$) δ 9.11 (d, J=1.8 Hz, 1H), 8.48 (s, 1H), 6.93 (t, JHF=53.7 Hz, 1H), 2.67 (s, 3H); $^{13}$C-NMR (150 MHz, CDCl$_3$) δ 194.7, 152.85 (t, JCF=23.5 Hz), 147.8, 141.3, 134.6, 119.6 (t, JCF=2.4 Hz), 112.4 (t, JCF=242.7 Hz), 27.2; $^{19}$F-NMR (376 MHz, CDCl$_3$) δ −118.7; IR (neat) ν=3051, 2924, 1692, 1582, 1398, 1355, 1286, 1251, 1192, 1102, 1035, 937, 921, 875, 795, 732 cm$^{-1}$. The characterization data are consistent with those reported for the trifluoromethyl analogue. [Ji et al., *Proc. Natl. Acad. Sci.*, 2011, 108:14411-14415.]

2-(difluoromethyl)-5-(1-methylpyrrolidin-2-yl)pyridine (10)

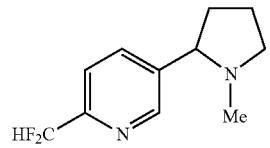

10

Standard Procedure B was followed with a reaction time of 24 hours (no second addition of reagents needed) to provide 10 in 36% yield as a colorless oil; Rf=0.33 (100% EtOAc); $^1$H-NMR (600 MHz, CDCl$_3$) δ 8.57 (d, J=2.0 Hz, 1H), 7.85 (dd, J=8.0, 2.0 Hz, 1H), 7.60 (d, J=8.1 Hz, 1H), 6.64 (t, JHF=55.6 Hz, 1H), 3.26 (ddd, J=9.6, 8.0, 2.1 Hz, 1H), 3.16 (t, J=8.4 Hz, 1H), 2.34 (q, J=9.1 Hz, 1H), 2.27-2.19 (m, 1H), 2.01 (s, 3H), 2.01-1.92 (m, 1H), 1.84 (dddd, J=15.1, 12.5, 6.8, 2.0 Hz, 1H), 1.75-1.65 (m, 1H); $^{13}$C-NMR (150 MHz, CDCl$_3$) δ 151.8 (t, JCF=25.5 Hz), 149.3, 141.5, 136.3, 120.2 (t, JCF=2.9 Hz), 114.2 (t, JCF=238.5 Hz), 68.7, 57.1, 40.6, 35.6, 22.9; $^{19}$F-NMR (376 MHz, CDCl$_3$) δ −115.5; IR (neat) ν=2945, 2780, 2359, 1453, 1372, 1200, 1085, 1036, 907, 841, 730 cm$^{-1}$; HRMS (ESI-TOF) calc'd for C$_{11}$H$_{15}$F$_2$N$_2$ [M+H] 213.1198. found 213.1200.

6-chloro-5-(difluoromethyl)pyridin-2 (1H)-one (11)

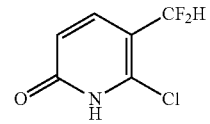

11

Standard Procedure B was followed with a reaction time of 24 hours (no second addition of reagents needed) to provide 11 in 62% yield as a white solid; Rf=0.40 (40% Diethylether/hexanes); m.p.: 79-81° C.; $^1$H-NMR (400 MHz, CDCl$_3$) δ 7.84 (d, J=7.8 Hz, 1H), 6.86 (t, JHF=56.0 Hz, 1H), 6.73-6.69 (m, 1H); $^{13}$C-NMR (150 MHz, CDCl$_3$) δ 162.7, 144.6, 139.8, 119.2 (t, JCF=23.0 Hz), 110.5 (t, JCF=236.0 Hz), 111.7; $^{19}$F-NMR (376 MHz, CDCl$_3$) δ −117.6; IR (neat) ν=2919, 2674, 1648, 1595, 1562, 1486, 1455, 1409, 1354, 1319, 1295, 1179, 1133, 1107, 1046, 1010, 956, 941, 839, 821, 806, 770 cm$^{-1}$; HRMS (ESI-TOF) calc'd for C$_6$H$_5$ClF$_2$NO [M+H] 180.0022. found 189.0023.

2-(difluoromethyl)isonicotinonitrile (12)

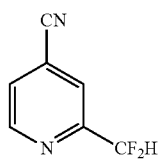

The Standard Procedure B was followed with a reaction time of 24 hours (no second addition of reagents needed) to provide 12 in 65% yield as white needles after sublimation upon standing at room temperature; Rf=0.33 (100% Dichloromethane); m.p.: 35° C.; $^1$H-NMR (600 MHz, CDCl$_3$) δ 8.87 (d, J=5.0 Hz, 1H), 7.88 (s, 1H), 7.73-7.59 (m, 1H), 6.68 (t, JHF=54.9 Hz, 1H); $^{13}$C-NMR (150 MHz, CDCl$_3$) δ 154.5 (t, JCF=26.6 Hz), 150.8, 127.1 (t, JCF=1.7 Hz), 122.2 (t, JCF=3.2 Hz), 122.1, 115.8, 112.9 (t, JCF=241.5 Hz); $^{19}$F-NMR (376 MHz, CDCl$_3$) δ −117.0; IR (neat) ν=3078, 2924, 2854, 2243, 2154, 2015, 1955, 1797, 1723, 1602, 1557, 1462, 1438, 1415, 1375, 1301, 1265, 1216, 1160, 1119, 1099, 1079, 1048, 994, 942, 901, 857, 797, 777, 735, 703, 685 cm$^{-1}$; HRMS (ESITOF) calc'd for C$_7$H$_5$F$_2$N$_2$ [M+H] 155.0415. found 155.0416.

5-(difluoromethyl)-1,3,4-thiadiazol-2-amine (13)

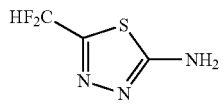

Standard Procedure A was followed with a reaction time of 24 hours (no second addition of reagents needed) to provide 13 in 40% yield as a solid; Rf=0.46 (80% EtOAc/hexanes); m.p.: 122-124° C.; $^1$H-NMR (400 MHz, CD$_3$OD) δ 6.93 (t, JHF=53.0 Hz, 1H); $^{13}$C-NMR (150 MHz, CD$_3$OD) δ 173.2, 153.1 (t, JCF=29.0 Hz), 112.2 (t, JCF=234.0 Hz); $^{19}$F-NMR (376 MHz, CD$_3$OD) δ −115.9; IR (neat) ν=3266, 3114, 2979, 2474, 2276, 1505, 1347, 1297, 1259, 1234, 1176, 1046, 908, 822 cm$^{-1}$; HRMS (ESI-TOF) calc'd for C$_3$H$_4$F$_2$N$_3$S [M+H] 152.0089. found 152.0087.

1-(2-(difluoromethyl)-1-methyl-1H-pyrrol-3-yl)ethanone (14)

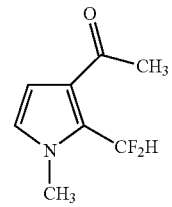

Standard Procedure B was followed with a reaction time of 8 hours, where a second addition of reagents was administered and allowed to stir for an additional 14 hours to provide 14 in 65% yield as a white foam; Rf=0.3 (50% dichloromethane/hexanes); $^1$H-NMR (400 MHz, CDCl$_3$) δ 7.59 (t, JHF=53.2 Hz, 1H), 6.62 (d, J=2.3 Hz, 1H), 6.47 (d, J=2.9 Hz, 1H), 3.82 (s, 3H), 2.43 (s, 3H); $^{13}$C-NMR (150 MHz, CDCl$_3$) δ 195.3, 127.3 (t, JCF=22.5 Hz), 125.5, 125.4 (t, JCF=4.5 Hz), 110.4, 109.6 (t, JCF=232.5 Hz), 36.2 (t, JCF=4.5 Hz), 28.5; $^{19}$F-NMR (376 MHz, CDCl$_3$) δ −113.3; IR (neat) ν=2962, 2919, 1662, 1553, 1509, 1364, 1254, 1061, 995 cm$^{-1}$; HRMS (ESI-TOF) calc'd for C$_8$H$_{10}$F$_2$NO [M+H] 174.0730. found 174.0725.

1-(5-(difluoromethyl)-1H-pyrrol-2-yl)ethanone (15)

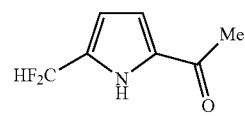

Standard Procedure B was followed with a reaction time of 24 hours (no second addition of reagents needed) to provide 15 in 55% yield as a white solid; Rf=0.70 (35% EtOAc/hexanes); m.p.: 88-90° C.; $^1$H-NMR (400 MHz, CDCl$_3$) δ 6.88 (dq, J=2.7, 1.3 Hz, 1H), 6.73 (t, JHF=55 Hz, 1H), 6.50-6.44 (m, 1H), 2.47 (s, 3H); $^{13}$C-NMR (150 MHz, CDCl$_3$) δ 189.0, 133.2, 130.7 (t, JCF=27.0 Hz), 117.2, 109.6 (t, JCF=234.0 Hz), 110.4, 25.8; $^{19}$F-NMR (376 MHz, CDCl$_3$) δ −111.7; IR (neat) ν=3247, 2035, 1645, 1376, 1228, 1094, 1012, 931, 805, 780 cm$^{-1}$; HRMS (ESI-TOF) calc'd for C$_7$H$_8$F$_2$NO [M+H] 160.0568. found 160.0574.

2-(difluoromethyl)-3-methylquinoxaline (16)

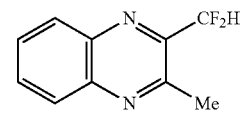

Standard Procedure B was followed with a reaction time of 24 hours (no second addition of reagents needed) to provide 16 in 50% yield as an off-white solid; Rf=0.75 (25% EtOAc/hexanes); m.p.: 109-111° C.; $^1$H-NMR (400 MHz, CDCl$_3$) δ 8.07 (app t, J=8.0 Hz, 2H), 7.86-7.73 (m, 2H), 6.83

(t, JHF=52.0 Hz, 1H), 2.93 (s, 3H); $^{13}$C-NMR (150 MHz, CDCl$_3$) δ 152.4, 145.9 (t, JCF=27.0 Hz), 142.6, 139.5, 131.7, 129.9, 129.5, 128.7, 116.7 (t, JCF=240.0 Hz), 21.9; $^{19}$F-NMR (376 MHz, CDCl$_3$) δ −111.7; IR (neat) ν=1563, 1489, 1376, 1183, 1125, 1072, 1038, 1009, 985, 962, 903, 766, 720 cm$^{-1}$; HRMS (ESI-TOF) calc'd for C$_{19}$H$_9$F$_2$N$_2$ [M+H] 195.0728. found 195.0725.

2-(difluoromethyl)-5,6-diethyl-3-methylpyrazine (17)

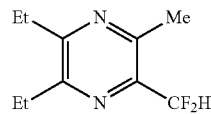

Standard Procedure A was followed with a reaction time of 17 hours (no second addition of reagents needed) to provide 17 in 66% yield as a yellow oil; Rf=0.14 (25% dichloromethane/hexanes); $^1$H-NMR (400 MHz, CDCl$_3$) δ 6.66 (t, JHF=55.0 Hz, 1H), 2.90-2.78 (m, 4H), 2.66 (s, 3H), 1.29 (td, J=7.5, 4.0 Hz, 6H); $^{13}$C-NMR (150 MHz, CDCl$_3$) δ 157.4, 152.3, 142.2 (t, JCF=21.0 Hz), 116.8 (t, JCF=238.5 Hz), 27.7, 26.9, 20.3, 13.2, 12.9; $^{19}$F-NMR (376 MHz, CDCl$_3$) δ −114.6; IR (neat) ν=2974, 2927, 1664, 1461, 1427, 1347, 1040, 779 cm$^{-1}$; HRMS (ESI-TOF) calc'd for C$_{10}$H$_{15}$F$_2$N$_2$ [M+H] 201.1198. found 201.1196.

methyl 4-(difluoromethyl)pyrimidine-2-carboxylate (18-4C) and methyl 5-(difluoromethyl)pyrimidine-2-carboxylate (18-5C)

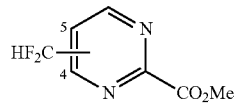

Standard Procedure A was followed with a reaction time of 12 hours (no second addition of reagents needed) to provide 18 in 62% yield (C4:C5 4:1).

Data for 18-4C: yellow oil; Rf=0.20 (60% EtOAc/hexanes); $^1$H-NMR (400 MHz, CDCl$_3$) δ 9.15 (d, J=5.0 Hz, 1H), 7.82 (d, J=5.0 Hz 1H), 6.70 (t, JHF=54.5 Hz, 1H), 4.10 (s, 3H); $^{13}$C-NMR (150 MHz, CDCl$_3$) δ 163.2, 161.6 (t, JCF=27.0 Hz), 160.0, 156.6, 119.0, 112.2 (t, JCF=241.5 Hz), 54; $^{19}$F-NMR (376 MHz, CDCl$_3$) δ −119.0; IR (neat) ν=3013, 2921, 2851, 1727, 1592, 1562, 1334, 1152, 1102, 954, 821 cm$^{-1}$; HRMS (ESI-TOF) calc'd for C$_7$H$_7$F$_2$N$_2$O$_2$ [M+H] 189.0470. found 189.0472.

Data for 18-5C: white solid; Rf=0.19 (60% EtOAc/hexanes); m.p.: 94-97° C.; $^1$H-NMR (400 MHz, CDCl$_3$) δ 9.08 (s, 2H), 6.86 (t, JHF=54.9 Hz, 1H), 4.10 (s, 3H); $^{13}$C-NMR (150 MHz, CDCl$_3$) δ 163.1, 158.0, 155.8, 129.8 (t, JCF=24.0 Hz), 111.6 (t, JCF=240 Hz), 54.0; $^{19}$F-NMR (376 MHz, CDCl$_3$) δ −115.5; IR (neat) ν=3013, 2921, 2851, 1727, 1592, 1562, 1334, 1152, 1102, 954, 821 cm$^{-1}$.

8-(difluoromethyl)-3,7-dimethyl-1-(5-oxohexyl)-1H purine-2,6 (3H,7H)-dione (19)

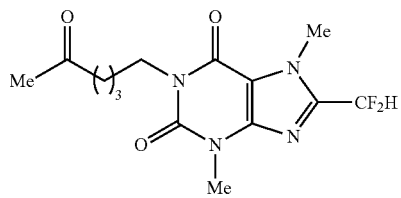

Standard Procedure A was followed with a reaction time of 22 hour (no second addition of reagents needed) to provide 19 in 72% yield as a white solid; Rf=0.30 (30% EtOAc/hexanes); m.p.: 102-104° C.; $^1$H-NMR (400 MHz, CDCl$_3$) δ 6.72 (t, JHF=52.0 S-16 Hz, 1H), 4.10 (s, 3H), 4.02-3.92 (m, 2H), 3.50 (s, 3H), 2.46 (t, J=6.9 Hz, 2H), 2.10 (s, 3H), 1.60 (app d, J=3.8 Hz, 4H); $^{13}$C-NMR (150 MHz, (CDCl$_3$) δ 208.6, 155.4, 151.2, 146.9, 142.9 (t, JCF=26.5 Hz), 109.8 (t, JCF=237.0 Hz), 109.6, 43.1, 41.0, 32.9, 30.0, 29.7, 27.4, 20.9; $^{19}$F-NMR (376 MHz, CDCl$_3$) δ −115.4; IR (neat) ν=2952, 2359, 1698, 1603, 1545, 1446, 1331, 1283, 1216, 1159, 1097, 1041, 965, 881, 852, 798, 763, 748 cm$^{-1}$; HRMS (ESI-TOF) calc'd for C$_{14}$H$_{19}$F$_2$NO$_4$ 329.1420. found 329.1420.

8-(difluoromethyl)-1,3-dimethyl-1H-purine-2,6(3H, 7H)-dione (20)

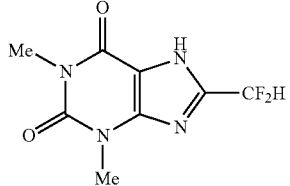

Standard Procedure A was followed with a reaction time of 16 hours (no second addition of reagents needed) to provide 20 in 90% yield as a white solid; Rf=0.60 (80% EtOAc/hexanes); decomposition 145° C.; $^1$H-NMR (400 MHz, DMSO-d$_6$) δ 7.10 (t, JHF=53.0 Hz, 1H), 3.40 (s, 3H), 3.21 (s, 3H); $^{13}$C-NMR (150 MHz, DMSO-d$_6$) δ 154.7, 151.1, 147.2, 143.4 (t, JCF=29.0 Hz), 108.8 (t, JCF=236.0 Hz), 108.4, 29.9, 27.9; $^{19}$F-NMR (376 MHz, DMSO-d$_6$) δ −115.3; IR (neat) ν=2956, 1705, 1663, 1548, 1455, 1427, 1336, 1288, 1224, 1088, 1036, 976, 820, 762, 732 cm$^{-1}$; HRMS (ESI-TOF) calc'd for C$_8$H$_9$F$_2$N$_4$O$_2$ [M+H] 231.0688. found 231.0697.

8-(difluoromethyl)-1,3,7-trimethyl-1H-purine-2,6 (3H,7H)-dione (2). 0.25 mmol-scale procedure

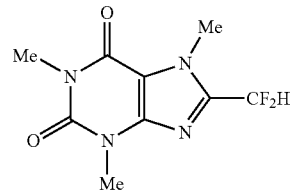

Standard Procedure A was followed with a reaction time of 5 hours (no second addition of reagents needed) to provide 2 in 73% yield.

Gram-Scale Procedure:

To a stirred solution of caffeine (1.00 g, 5.15 mmol, 1.0 equiv) and DFMS (4.57 g, 15.45 mmol, 3.0 equiv) in dichloromethane (10.3 mL) and water (4.1 mL) at 0° C. and open to air was added tert-butyl hydroperoxide (70% solution in water, 3.50 mL, 25.75 mmol, 5.0 equiv) via syringe pump (0.1 mL/min) over 35 minutes. The reaction mixture was removed from the ice bath and allowed to warm to room temperature where it was stirred for 4 hours. The reaction mixture was partitioned between dichloromethane (150 mL) and saturated sodium bicarbonate (125 mL). The organic layer was separated, and the aqueous layer was extracted with dichloromethane (3×20 mL). The combined organic layers were dried over $Na_2SO_4$.

The crude material was dissolved in a minimal amount of DCM and loaded onto silica gel. Elution with 15%-30% EtOAc/hexanes followed by removal of the solvent gave 2 as a white solid (915 mg) 73% yield; Rf=0.55 (60% EtOAc/hexanes); m.p.: 157-160° C.; $^1$H-NMR (400 MHz, $CDCl_3$) δ 6.73 (t, JHF=52.2 Hz, 1H), 4.12 (s, 3H), 3.52 (s, 3H), 3.36 (s, 3H); $^{13}$C-NMR (150 MHz, ($CDCl_3$) δ 155.6, 151.5, 147.0, 142.9 (t, JCF=27.0 Hz), 109.8 (t, JCF=237.0 Hz), 109.5, 33.0, 32.9, 29.8, 28.2; $^{19}$F-NMR (376 MHz, $CDCl_3$) δ −115.3; IR (neat) v=2956, 1705, 1663, 1548, 1455, 1427, 1336, 1288, 1224, 1088, 1037, 976, 820, 762, 732 cm$^{-1}$; HRMS (ESI-TOF) calc'd for $C_9H_{11}F_2N_4O_2$ [M+H] 245.0845. found 245.0853.

6-chloro-2,8-bis(difluoromethyl)-9H-purine (21)

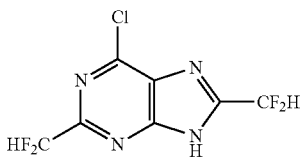

To a solution of heterocycle (0.25 mmol, 1.0 equiv) and DFMS (173 mg, 0.50 mmol, 3.0 equiv) in dichloromethane (1.0 mL) and water (0.4 mL) at rt was added drop-wise tert-butyl hydroperoxide (70% solution in water, 0.1 mL, 0.16 mmol, 4.0 equiv) with vigorous stirring. The reaction was monitored by thin layer chromatography until completion. Upon consumption of starting material, the reaction was partitioned between dichloromethane (2.0 mL) and saturated sodium bicarbonate (2.0 mL). The organic layer was separated, and the aqueous layer was extracted with dichloromethane (3×2.0 mL). The organic layers were dried with sodium sulfate, concentrated and purified by column chromatography on silica gel to provide 21 in 30% yield as a colorless oil; Rf=0.30 (50% EtOAc/hexanes); $^1$H-NMR (400 MHz, $CDCl_3$) δ 7.00 (t, JHF=52.8 Hz, 1H), 6.78 (t, JHF=54.4 Hz, 1H); $^{13}$C-NMR (150 MHz, $CDCl_3$) δ 156.2, 156.0, 155.8, 152.8, 149.3, 110.1 (t, JCF=243.0 Hz), 108.5 (t, JCF=240.0 Hz); $^{19}$F-NMR (376 MHz, $CDCl_3$) δ −117.1, −117.2; IR (neat) v=3159, 2925, 2854, 2159, 1675, 1611, 1574, 1518, 1459, 1386, 1345, 1284, 1264, 1219, 1108, 1064, 925, 864, 819, 737 cm$^{-1}$; HRMS (ESI-TOF) calc'd for $C_7H_4ClF_4N_4$ [M+H] 255.0055. found 255.0063.

6-chloro-2,8-bis(difluoromethyl)-9H-purine (22)

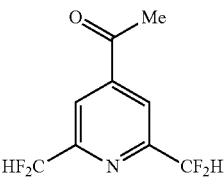

Standard Procedure B was followed with a reaction time of 24 hours (no second addition of reagents needed) to provide 22 in 50% yield as a yellow solid; Rf=0.30 (50% EtOAc/hexanes); Decomposition 139° C.; $^1$H-NMR (600 MHz, $CDCl_3$) δ 8.11 (s, 2H), 6.71 (t, JHF=13.5 Hz, 1H); $^{13}$C-NMR (175 MHz, $CDCl_3/CD_3OD$) δ 166.0, 153.9 (t, JCF=22.5 Hz), 144.2, 120.1, 113.11 (t, JCF=241.1 Hz); $^{19}$F-NMR (376 MHz, $CDCl_3$) δ −116.3; IR (neat) v=3377, 3203, 2946, 2880, 2157, 2019, 1677, 1610, 1573, 1421, 1360, 1264, 1220, 1120, 1046, 999, 908, 731, 704 cm$^{-1}$; HRMS (ESI-TOF) calc'd for $C_8H_7F_4N_2O$ [M+H]; 223.0489. found 223.0486.

2,4-bis(difluoromethyl)quinoline (23)

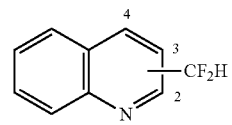

Standard Procedure A was followed with a reaction time of 17 hours (no second addition of reagents needed) to provide 23 in 30% yield as a brown-red oil; Rf=0.40 (50% dichloromethane/hexanes); $^1$H-NMR (400 MHz, $CDCl_3$) δ 8.52 (d, J=8.4 Hz, 1H), 8.15 (d, J=8.5 Hz, 1H), 7.93 (s, 1H), 7.87 (dd, J=8.5, 6.9 Hz, 1H), 7.78-7.72 (m, 1H), 7.20 (t, JHF=54.3 Hz, 1H), 6.81 (t, J=8.5 Hz, 1H); $^{13}$C-NMR (150 MHz, $CDCl_3$) δ 152.7 (t, JCF=27.0 Hz), 147.8, 140.0 (t, JCF=21.0 Hz), 130.9, 130.8, 129.4, 124.8, 123.6, 114.4 (t, JCF=240.0 Hz), 114.3, 113.1 (t, JCF=240.0 Hz); $^{19}$F-NMR (376 MHz, $CDCl_3$) δ −114.7, −115.4; IR (neat) v=3094, 2976, 1615, 1513, 1470, 1383, 1232, 1199, 1172, 1029, 903 cm$^{-1}$; HRMS (ESI-TOF) calc'd for $C_{11}H_8F_4N$ [M+H] 230.0587. found 230.0597.

2-((difluoromethyl)thio)-1-methyl-1H-imidazole (24)

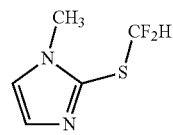

Standard Procedure B was followed with a reaction time of 16 hours (no second addition of reagents needed) to provide 24 in 69% yield as a yellow oil; Rf=0.21 (25%

EtOAc/hexanes); $^1$H-NMR (400 MHz, CDCl$_3$) δ 7.19 (d, J=1.3 Hz, 1H), 7.10 (d, J=1.3 Hz, 1H), 6.91 (t, JHF=57.3 Hz, 1H); $^{13}$C-NMR (150 MHz, CDCl$_3$) δ 132.2, 131.2, 125.0, 120.6 (t, JCF=277.5 Hz), 34.3; $^{19}$F-NMR (376 MHz, CDCl$_3$) δ −92.0; IR (neat) ν=1459, 1281, 1063, 455, 686 cm$^{-1}$; HRMS (ESI-TOF) calc'd for C$_5$H$_7$F$_2$N$_2$S [M+H] 165.0293. found 165.0290.

2-((difluoromethyl)thio)benzo[d]thiazole (25)

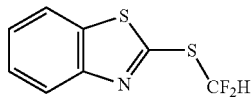

Standard Procedure B was followed with a reaction time of 16 hours (no second addition of reagents needed) to provide 25 in 61% yield as a yellow oil; Rf=0.47 (25% dichloromethane/hexanes); $^1$H-NMR (400 MHz, CDCl$_3$) δ 8.0 (d, J=8.1 Hz, 1H), 7.83 (d, J=7.8 Hz, 1H), 7.64 (t, JHF=55.8 Hz, 1H), 7.54-7.85 (m, 2H); $^{13}$C-NMR (150 MHz, CDCl$_3$) δ 157.2 (t, JCF=4.5 Hz), 153.0, 136.1, 126.8, 125.8, 123.0, 121.3, 120.4 (t, JCF=276.0 Hz); $^{19}$F-NMR (376 MHz, CDCl$_3$) δ −93.5. The characterization data are consistent with that reported. [Zhao et al., J. Org. Lett. 2010, 12, 1444-1447.]

2-((difluoromethyl)thio)benzo[d]oxazole (26)

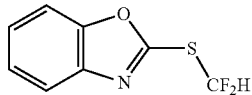

Standard Procedure B was followed with a reaction time of 16 hours (no second addition of reagents needed) to provide 26 in 56% yield as a yellow oil; Rf=0.29 (25% dichloromethane/hexanes); $^1$H-NMR (600 MHz, CDCl$_3$) δ 7.72 (t, JHF=54.0 Hz, 1H), 7.70-7.67 (m, 1H), 7.53-7.50 (m, 1H), 7.38-7.32 (m, 2H); $^{13}$C-NMR (150 MHz, CDCl$_3$) δ 157.4, 151.9, 141.4, 125.3, 125.1, 119.9 (t, JCF=276.0 Hz), 119.5, 110.5; $^{19}$F-NMR (376 MHz, CDCl$_3$) δ −93.5; IR (neat) ν=1511, 1453, 1234, 1138, 1070, 806, 781, 744 cm$^{-1}$; HRMS (ESI-TOF) calc'd for C$_8$H$_6$F$_2$NOS [M+H] 202.0133. found 202.0130.

3-(difluoromethyl)cyclohexanone (27)

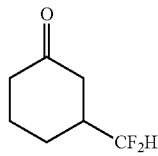

To a solution of cyclohexenone (0.25 mmol, 1.0 equiv) and DFMS (87 mg, 0.25 mmol, 1.0 equiv) in dichloromethane (1.0 mL) and water (0.4 mL) at room temperature was added drop-wise tert-butyl hydroperoxide (70% solution in water, 52 μL, 0.38 mmol, 1.5 equiv) with vigorous stirring. The reaction was monitored by thin layer chromatography until completion. Upon consumption of starting material, the reaction was partitioned between dichloromethane (2.0 mL) and water (2.0 mL). The organic layer was separated, and the aqueous layer was extracted with dichloromethane (3×2.0 mL). The organic layers were dried with sodium sulfate, concentrated and purified by column chromatography on silica gel to provide 27 in 40% yield as a colorless oil; Rf=0.25 (15% EtOAc/hexanes); $^1$H-NMR (400 MHz, CDCl$_3$) δ 5.70 (dt, JHF=56.0 Hz, 4.0, 1H), 2.53-2.47 (m, 1H), 2.46-2.38 (m, 1H), 2.35-2.21 (m, 3H), 2.19-2.10 (m, 1H), 2.04-1.96 (m, 1H), 1.75-1.53 (m, 2H); $^{13}$C-NMR (100 MHz, CDCl$_3$) δ 209.0, 117.3 (t, JCF=235.0 Hz), 42.3 (t, JCF=20.0 Hz), 41.3, 40.1 (t, JCF=6.0 Hz), 24.4, 24.0 (t, JCF=4.0 Hz); $^{19}$F-NMR (376 MHz, CDCl$_3$) δ-122.3-126.2 (m) IR (neat) ν=2953, 1711, 1606, 1563, 1508, 1453, 1421, 1264, 1226, 1193, 1107, 1025, 998, 975, 952, 910, 875, 765 cm$^{-1}$; HRMS (ESI-TOF) calc'd for C$_7$H$_{11}$F$_2$O [M+H] 149.0778. found 149.0782.

2-(difluoromethyl)chroman-4-one (28)

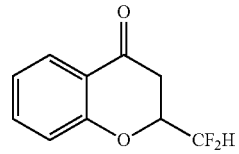

To a solution of heterocycle (0.25 mmol, 1.0 equiv) and zinc difluoromethanesulfinate (DFMS) (173 mg, 0.50 mmol, 2.0 equiv) in α, α, α-trifluorotoluene (1.0 mL) and water (0.4 mL) at room temperature was slowly added tert-butyl hydroperoxide (70% solution in water, 0.1 mL, 0.75 mmol, 3.0 equiv) with vigorous stirring for 24 hours, where a second addition of DFMS (2.0 equiv) and tert-butyl hydroperoxide (3.0 equiv) was then added to drive the reaction further. Upon consumption of starting material, the reaction was partitioned between dichloromethane (2.0 mL) and water (2.0 mL). The organic layer was separated, and the aqueous layer was extracted with dichloromethane (3×2.0 mL). The organic layers were dried with sodium sulfate, concentrated and purified by column chromatography on silica gel. 28 provided in 30% yield as a white solid; Rf=0.27 (50% dichloromethane/hexanes); m.p.: 36-38° C.; $^1$H-NMR (400 MHz, CDCl$_3$) δ 7.91 (dd, J=7.8 Hz, 1H), 7.53 (ddd, J=8.6, 7.3, 1.8 Hz, 1H), 7.15-6.94 (m, 2H), 6.04 (ddd, JHF=55.6, 54.2, 3.3 Hz, 1H), 4.77-4.53 (m, 1H), 3.00-2.80 (m, 2H); $^{13}$C-NMR (150 MHz, CDCl$_3$) δ 189.6, 160.1, 136.6, 127.2, 122.5, 121.0, 118.0, 113.6 (app t, JCF=241.5 Hz), 75.8 (dd, JCF=28.5, 26.2 Hz), 35.8 (t, JCF=2.8 Hz); $^{19}$F-NMR (376 MHz, CDCl$_3$) δ −127.7-133.2 (m). IR (neat) ν=2919, 1694, 1604, 1461, 1299, 1067, 932 cm$^{-1}$; HRMS (ESI-TOF) calc'd for C$_{10}$H$_9$F$_2$O$_2$ [M+H] 199.0565. found 199.0560.

(Z)-4-(difluoromethyl)-3-(1-hydroxyethylidene)-chroman-2-one (29-enol) and 3-acetyl-4-(difluoromethyl)-chroman-2-one (29-keto)

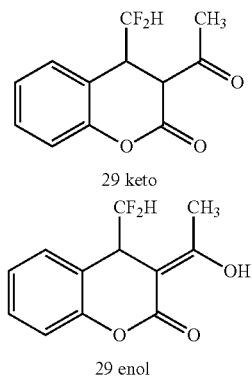

29 keto 29 enol

To a solution of heterocycle (0.25 mmol, 1.0 equiv) and zinc difluoromethanesulfinate (DFMS) (173 mg, 0.50 mmol, 2.0 equiv) in α, α, α-trifluorotoluene (1.0 mL) and water (0.4 mL) at room temperature was slowly added tert-butyl hydroperoxide (70% solution in water, 0.1 mL, 0.75 mmol, 3.0 equiv) with vigorous stirring for 12 hours, where a second addition of DFMS (2.0 equiv) and tert-butyl hydroperoxide (3.0 equiv) was then added to drive the reaction further. Upon consumption of starting material, the reaction was partitioned between dichloromethane (2.0 mL) and water (2.0 mL). The organic layer was separated, and the aqueous layer was extracted with dichloromethane (3×2.0 mL). The combined organic layers were dried with sodium sulfate, concentrated and purified by column chromatography on silica gel provided 29 in 40% yield as a colorless oil; Rf=0.21 (50% dichloromethane/hexanes). Both major (enol) and minor (keto) peaks are listed for both $^1$H and $^{13}$C; $^1$H NMR (600 MHz, CDCl$_3$) δ 7.35 (td, J=7.8, 1.6 Hz, 1.2H), 7.31-7.2 (m, 1.2H), 7.22-7.16 (m, 1.2H), 7.11 (dd, J=8.2, 1.2 Hz, 1H), 7.07 (dd, J=8.2, 0.2 Hz, 0H), 5.94 (td, JHF=55.5, 2.8 Hz, 0.2H), 5.67 (td, JHF=56.3, 4.1 Hz, 1H), 4.12-4.06 (m, 1.2H), 3.98-3.86 (m, 0.2H), 2.33 (s, 0.6H), 2.23 (s, 3H); $^{13}$C NMR (150 MHz, CDCl$_3$) δ 197.4, 180.7, 169.3, 163.5, 151.4, 151.2, 130.5, 130.1, 129.8, 129.46, 125.5, 125.1, 117.5, 117.3, 116.4 (t, JCF=247.5 Hz), 88.9, 53.2, 53.2, 53.1, 42.5, 42.3, 42.1, 42.1, 42.0, 41.80, 28.3, 19.6; $^{19}$F-NMR (376 MHz, CDCl$_3$) δ −119.8-1124.2 (m). IR (neat) ν=2967, 1769, 1657, 1587, 1243, 1184, 1048, 954, 850 cm$^{-1}$; HRMS (ESI-TOF) calc'd for C$_{12}$H$_{11}$F$_2$O$_3$ [M+H] 241.0671. found 241.0665.

(1R)-(2-(difluoromethyl)-6-methoxyquinolin-4-yl) (5-ethylquinuclidin-2-yl)methanol (30) TFA salt

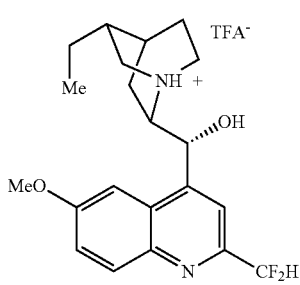

Standard Procedure A was followed with a reaction time of 18 hours (no second addition of reagents needed) to provide 30 after preparative HPLC purification (5% to 50% MeCN in H$_2$O, 0.1% TFA, 25 min ramp) as the TFA salt in 44% yield as a yellow oil; Rf=0.40 (10% methanol/dichloromethane); $^1$H-NMR (600 MHz, CD$_3$OD) δ 7.86 (d, J=9.3 Hz, 1H), 7.81 (s, 1H), 7.33-7.28 (m, 1H), 7.20 (s, 1H), 6.63 (t, JHF=55.3 Hz, 1H), 5.95 (s, 1H), 3.81 (s, 4H), 3.44 (t, J=9.5 Hz, 1H), 3.16-3.08 (m, 3H), 2.25 (dd, J=13.7, 9.1 Hz, 1H), 1.81 (s, 1H), 1.77-1.61 (m, 3H), 1.46 (ddd, J=24.7, 14.3, 7.0 Hz, 2H), 1.04-0.96 (m, 1H), 0.78 (t, J=7.4 Hz, 3H); $^{13}$C-NMR (150 MHz, CD$_3$OD) δ 161.2, 151.2 (t, JCF=25.5 Hz), 148.6, 144.4, 132.6, 128.0, 124.6, 115.9 (t, JCF=238.5 Hz), 115.8, 101.7, 68.6, 61.2, 56.7, 51.5, 50.5, 36.2, 26.4, 25.4, 24.6, 18.6, 11.8; $^{19}$F-NMR (376 MHz, CD$_3$OD) δ −76.9; IR (neat) ν=3283 (br), 2964, 1669, 1478, 116, 1023, 834 cm$^{-1}$; HRMS (ESI-TOF) calc'd for C$_{21}$H$_{27}$F$_2$N$_2$O$_2$ [M+H] 377.2035. found 377.2050.

(6S,10R)-2-(difluoromethyl)-7,8,9,10-tetrahydro-6H-6,10-methanoazepino[4,5-g]quinoxaline (31) TFA salt

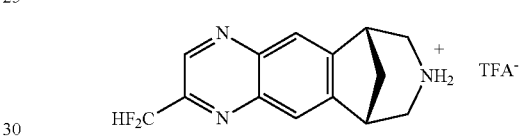

Standard Procedure A was followed with a reaction time of 18 hours (no second addition of reagents needed) to provide 31 after preparative HPLC purification (5% to 50% MeCN in H$_2$O, 0.1% TFA, 25 min ramp) as the TFA salt in 50% yield as a yellow solid; Rf=0.16 (10% methanol/dichloromethane); decomposition: 250° C.; $^1$H-NMR (400 MHz, D$_2$O) δ 8.98 (s, 1H), 7.88 (d, J=11.2 Hz, 2H), 6.97 (t, JHF=54.0 Hz, 1H), 3.65 (dt, J=4.5, 2.1 Hz, 2H), 3.48 (d, J=12.4 Hz, 2H), 3.31 (d, J=12.4 Hz, 2H), 2.52-2.38 (m, 1H), 2.19 (d, J=11.9 Hz, 1H); $^{13}$C-NMR (150 MHz, D$_2$O) δ 149.1, 148.5, 147.8 (t, JCF=25.5 Hz), 144.1, 142.7, 142.4, 124.5, 124.3, 113.8 (t, JCF=238.5 Hz), 48.6, 41.2, 39.7, 39.6; $^{19}$F-NMR (376 MHz, D$_2$O) δ −75.7; IR (neat) ν=1664, 1459, 1367, 1181, 1131, 1096, 1032, 835, 794, 719 cm$^{-1}$; HRMS (ESI-TOF) calc'd for C$_{14}$H$_{13}$F$_2$N$_3$ [M+H] 262.1156. found 262.1161.

4-Chloro-2-(difluoromethyl)pyridine (32)

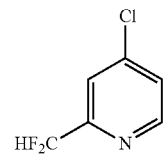

Standard Procedure A (0.25 mmol, 1.0 mL DCM/0.4 mL H$_2$O) was followed with a reaction time of 12 hours to provide 32 in 51% yield (very volatile! NMR yield based on internal standard of 1,4-dimethoxybenzene) as a yellow oil; Rf=0.55 (20% EtOAc/hexanes); $^1$H-NMR (500 MHz, CDCl$_3$) δ 8.55 (d, J=5.3 Hz, 1H), 7.65 (d, J=1.9 Hz, 1H), 7.44-7.39 (m, 1H), 6.61 (t, J=55.2 Hz, 1H); $^{13}$C-NMR (125

MHz, CDCl$_3$) δ 154.4 (t, JCF=26.2 Hz), 150.6, 145.7, 125.9, 121.0 (t, JCF=3.6 Hz), 113.3 (t, JCF=241.7 Hz); $^{19}$F-NMR (376 MHz, CDCl$_3$) δ −116.8; IR (neat) v=2982, 1613, 1481, 1360, 1314, 1137, 1088, 962 cm$^{-1}$; HRMS (ESI-TOF) calc'd for C$_6$H$_4$ClF$_2$N [M+H] 164.0073. found 164.0078.

2-(2-(Difluoromethyl)-6-(trifluoromethyl)pyridin-4-yl)acetic acid (33)

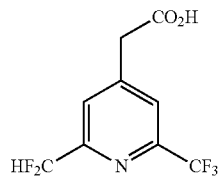

To a vigorously stirred solution of 4-pyridylacetic acid hydrochloride (110 mg, 0.634 mmol, 1.0 equiv) and zinc trifluoromethanesulfinate (TFMS; 413 mg, 1.25 mmol, 2.0 equiv) in DCM (2.5 mL) and water (1.0 mL) at 0° C. was added tert-butyl hydroperoxide (70% solution in water, 255 μL, 1.8 mmol, 2.8 equiv) dropwise via Eppendorf pipette. The reaction mixture was stirred at room temperature for 12 hours followed by removal of the organic layer by pipette. The organic layer was dried over magnesium sulfate, filtered, concentrated in vacuo, precipitated with hexanes, decanted, and further dried in vacuo.

To a vigorously stirred, uniform suspension of the crude product and zinc difluoromethanesulfinate (DFMS; 92 mg, 0.31 mmol, 0.50 equiv) in perfluorotoluene (2.5 mL) and water (1.0 mL) at 0° C. was added tert-butyl hydroperoxide (70% solution in water, 64 μL, 0.45 mmol, 0.70 equiv) dropwise via Eppendorf pipette. The reaction mixture was stirred at 50° C. for 6 hours, cooled to 0° C. then charged with a second addition of reagents DFMS (92 mg, 0.31 mmol, 0.50 equiv) and tert-butyl hydroperoxide (70% solution in water, 64 μL, 0.45 mmol, 0.70 equiv). The reaction mixture was stirred for an additional 12 hours at 50° C. followed by cooling to 0° C., charging with a third addition of DFMS (372 mg, 1.26 mmol, 2.0 equiv) and tert-butyl hydroperoxide (70% solution in water, 255 μL, 1.8 mmol, 2.8 equiv) then stirred an additional 6 hours at 50° C. The reaction mixture was cooled to room temperature, diluted with saturated NaHCO$_3$ (15 mL), extracted with EtOAc (3×15 mL), dried over MgSO$_4$, filtered, and concentrated in vacuo. The crude product was purified by preparative TLC eluting with 50% Et$_2$O/hexanes to provide 33 (31 mg, 20%) as a white solid; Rf=0.70 (50% Et$_2$O/hexanes +1% AcOH); m.p.=73-78° C.; $^1$H-NMR (400 MHz, CDCl$_3$) δ 7.79 (s, 1H), 7.75 (s, 1H), 6.69 (t, J=54.9 Hz, 1H), 3.85 (s, 2H); $^{13}$C-NMR (150 MHz, CDCl$_3$) δ 174.2, 154.0 (t, JCF=27.1 Hz), 148.6 (q, JCF=35.5 Hz), 146.0, 124.0, 123.4 (q, JCF=2.7 Hz), 121.1 (q, JCF=274.3 Hz), 113.2 (t, JCF=241.5 Hz), 40.2; $^{19}$F-NMR (376 MHz, CDCl$_3$) δ −68.3, −116.1; IR (neat) v=3102, 1716, 1414, 1337, 1244, 1126, 1037, 918 cm$^{-1}$; HRMS (ESITOF) calc'd for C$_9$H$_7$F$_5$NO$_2$ [M+H] 256.0391. found 256.0388.

Ethyl 2-cyclohexyl-6-(difluoromethyl)isonicotinate (34)

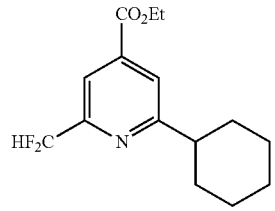

To a solution of ethyl isonicotinate (36.6 μL, 0.244 mmol, 1.0 equiv) and DFMS (200 mg, 0.677 mmol, 2.8 equiv) in 1,2-dichloroethane (1.0 mL) and water (0.4 mL) at 0° C. was added tert-butyl hydroperoxide (70% solution in water, 170 μL, 1.20 mmol, 5 equiv) drop-wise via Eppendorf pipette. The reaction mixture was stirred vigorously at room temperature for 2 hours followed by the addition zinc cyclohexylsulfinate (180 mg, 0.500 mmol, 2 equiv), TFA (20 μL, 0.261 mmol, 1.1 equiv), 1,2-dichloroethane (0.5 mL), and water (0.2 mL). The reaction mixture was cooled to 0° C. and tert-butyl hydroperoxide (70% solution in water, 102 μL, 0.72 mmol, 3.0 equiv) was added via Eppendorf pipette. The reaction mixture was stirred at 50° C. for 16 hours, cooled to 0° C. then charged with a second addition of reagents zinc cyclohexylsulfinate (180 mg, 0.500 mmol, 2 equiv) and tert-butyl hydroperoxide (70% solution in water, 102 μL, 0.72 mmol, 3.0 equiv). The reaction mixture was then stirred at 50° C. for 12 hours, cooled to 0° C., charged with a final addition of reagents zinc cyclohexylsulfinate (180 mg, 0.500 mmol, 2 equiv) and tert-butyl hydroperoxide (70% solution in water, 102 μL, 0.72 mmol, 3.0 equiv)) followed by stirring at 50° C. for 12 hours. The reaction mixture was cooled to room temperature, diluted with saturated NaHCO$_3$ (15 mL), extracted with EtOAc (3×15 mL), dried over MgSO$_4$, filtered, and concentrated in vacuo. The crude product was purified by preparative TLC eluting with 20% EtOAc/hexanes to give 34 (15.5 mg, 22% yield) and the 2,5-substituted regioisomer 34-C2,5 (4 mg, 6% yield).

Data for 34: Rf=0.51 (10% EtOAc/hexanes); $^1$H-NMR (400 MHz, CDCl$_3$) δ 7.98 (d, J=1.2 Hz, 1H), 7.82 (d, J=1.0 Hz, 1H), 6.65 (t, J=55.5 Hz, 1H), 4.43 (q, J=7.2 Hz, 2H), 2.82 (tt, J=11.9, 3.4 Hz, 1H), 2.01-1.93 (m, 2H), 1.87 (br dt, J=13.3, 3.4 Hz, 2H), 1.79-1.74 (m, 1H), 1.60-1.20 (m, 8H); $^{13}$C-NMR (150 MHz, CDCl$_3$) δ 168.1, 165.0, 153.2 (t, JCF=26.1 Hz), 139.6, 122.3, 116.9 (t, JCF=3 Hz), 114.0 (t, JCF=254 Hz), 62.2, 46.4, 32.8, 26.5, 26.0, 14.4. $^{19}$F-NMR (376 MHz, CDCl$_3$) δ −115.9; IR (neat) v=2977, 1609, 1573, 1523, 1385, 1273, 1095, 1051, 920 cm-1; HRMS (ESI-TOF) calc'd for C$_{15}$H$_{19}$F$_2$NO$_2$ [M+H] 284.1457. found 284.1470;

Data for 34-C2,5: Rf=0.37 (10% Et$_2$O/hexanes); $^1$H NMR (600 MHz, CDCl$_3$) δ 8.71 (s, 1H), 7.85 (s, 1H), 6.65 (t, J=55.4, 1H), 4.42 (q, J=7.1, 2H), 3.38-3.16 (m, 1H), 1.96-1.85 (m, 3H), 1.85-1.73 (m, 1H), 1.54-1.15 (m, 9H); $^{13}$C-NMR (150 MHz, CDCl$_3$) δ 166.3, 150.6 (t, JCF=25.7 Hz), 149.6, 143.9, 138.9, 119.6 (t, JCF=2.9 Hz), 113.8 (t, JCF=239.4 Hz), 62.2, 39.1, 34.0, 26.9, 26.0, 14.3; $^{19}$F-NMR (376 MHz, CDCl$_3$) δ −116.0; IR (neat) v=2928, 2854, 1728, 1449, 1377, 1271, 1210, 1091, 1043 cm$^{-1}$; HRMS (ESI-TOF) calc'd for C$_{15}$H$_{19}$F$_2$NO$_2$ [M+H] 284.1457. found 284.1465.

6-Chloro-2-(difluoromethyl)-8-isopropyl-7H-purine (35)

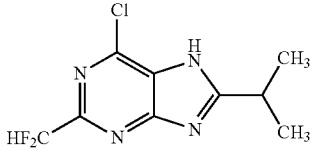

To a vigorously stirred suspension of 6-chloropurine (39 mg, 0.25 mmol, 1.0 equiv) and zinc isopropylsulfinate (IPS; 140 mg, 0.477 mmol, 2.0 equiv) in 1,2-dichloroethane (5 mL) and water (2.0 mL) at 0° C. was added tert-butyl hydroperoxide (70% solution in water, 102 μL, 0.72 mmol, 3 equiv) drop-wise via Eppendorf pipette. The reaction mixture was stirred at 50° C. for 12 hours, cooled to 0° C., charged with a second addition of reagents IPS (140 mg, 0.477 mmol, 2.0 equiv) and tert-butyl hydroperoxide (70% solution in water, 102 μL, 0.72 mmol, 3 equiv)), warmed to 50° C., stirred for 12 hours, cooled to 0° C., charged with a third addition of reagents IPS (140 mg, 0.477 mmol, 2.0 equiv) and tert-butyl hydroperoxide (70% solution in water, 102 μL, 0.72 mmol, 3 equiv)) and stirred for an additional 12 hours. The reaction mixture was diluted with saturated NaHCO$_3$ (15 mL), extracted with EtOAc (3×10 mL), the organic layer dried over MgSO$_4$, filtered, and concentrated in vacuo.

To a vigorously stirred solution of the resulting crude product, DFMS (222 mg, 0.751 mmol, 3 equiv), and TFA (30 μL 0.39 mmol, 1.6 equiv) in 1,2-dichloroethane (1.0 mL) and water (0.4 mL) at 0° C. was added tert-butyl hydroperoxide (70% solution in water, 170 μL, 1.20 mmol, 5.0 equiv) drop-wise via Eppendorf pipette. The reaction mixture was stirred at 50° C. for 24 hours, cooled to room temperature, diluted with saturated NaHCO$_3$ (15 mL), extracted with EtOAc (3×5 mL), the organic layer dried over MgSO$_4$, filtered, and concentrated in vacuo. The crude product was purified by preparative TLC eluting with 50% EtOAc/hexane to give 35 (14 mg, 23% yield) as a white solid; Rf=0.71 (60% EtOAc/hexanes); m.p.=146-149° C.; $^1$H-NMR (400 MHz, CDCl$_3$) δ 6.73 (t, J=54.7 Hz, 1H), 3.39 (hept, J=7.0 Hz, 1H), 1.51 (d, J=7.0 Hz, 6H); $^{13}$C-NMR (150 MHz, CDCl$_3$) δ 173.3, 150.9, 148.9 (q, JCF=34.3 Hz), 148.3, 129.3, 123.1 (q, JCF=2.9 Hz), 123.0 (q, JCF=273.3 Hz), 40.1; $^{19}$F-NMR (376 MHz, CDCl$_3$) δ −115.9; IR (neat) ν=2979, 2360, 1610, 1573, 1522, 1385, 1273, 1196, 1111, 1049, 920 cm$^{-1}$; HRMS (ESI-TOF) calc'd for C$_9$H$_{10}$ClF$_2$N$_4$ [M+H] 247.0557. found 247.0556.

6-Chloro-4-(difluoromethyl)-3-methoxypyridazine (36-C4) and 6-chloro-5-(difluoromethyl)-3-methoxypyridazine (36-C5)

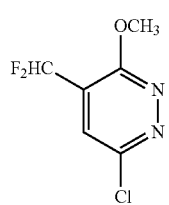

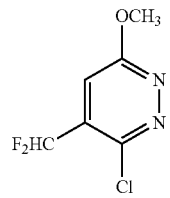

Standard Procedure A was utilized (0.25 mmol, 1.0 mL perfluorohexane/0.4 mL H$_2$O) was followed with a reaction time of 24 hours to provide 36-C4 and 36-C5 (6:1; C4:C5) as an inseparable mixture) in a combined yield of 57% (volatile) as a colorless oil.

Rf=0.29 (67% CH$_2$Cl$_2$/hexanes); (All proton signals listed) $^1$H-NMR (400 MHz, CD$_2$Cl$_{32}$) δ 7.61 (s, 1H), 7.25 (, 0.3; H), 6.78 (t, J=56.0 Hz, 0.3; H), 6.76 (t, J=56.0 Hz, 1H), 4.19 (s, 3H), 4.16 (s, 1H); $^{13}$C-NMR (100 MHz, CDCl$_3$) δ 165.0, 161.1 (t, JCF=4.9 Hz), 151.5, 147.8 (t, JCF=4.7 Hz), 134.6 (t, JCF=24.6 Hz), 126.9 (t, JCF=6.2 Hz), 125.0 (t, JCF=242.4 Hz), 116.7 (t, JCF=6.6 Hz), 110.6 (t, JCF=242.4 Hz), 55.9, 55.7; $^{19}$F-NMR (376 MHz, CDCl$_3$) δ −120.8 (C5), −121.4 (C4); IR (neat) ν=1464, 1375, 1324, 1156, 1068, 1004, 908 cm$^{-1}$; HRMS (ESI-TOF) calc'd for C$_6$H$_6$ClF$_2$N$_2$O [M+H] 195.0131. found 195.0129.

4-(Difluoromethyl)pyrimidine-2-carbonitrile (37-C4) and 5-(difluoromethyl)pyrimidine-2-carbonitrile (37-C5)

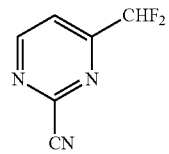

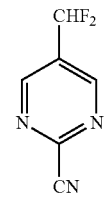

Standard Procedure A (0.25 mmol, 1.0 mL perfluorohexane/0.4 mL H$_2$O) was followed with a reaction time of 24 hours to provide 37-C4 and 37-C5 (1.6:1 C4:C5 from GC-MS, see below) in 21% combined yield (very volatile).

37-C4: Rf=0.38 (25% EtOAc/hexanes); $^1$H-NMR (400 MHz, CDCl$_3$) δ 9.08 (d, J=5.1 Hz, 1H), 7.84 (d, J=5.0 Hz, 1H), 6.60 (t, J=54.2 Hz, 1H); $^{13}$C-NMR (150 MHz, CDCl$_3$) δ 161.9 (t, JCF=28.1 Hz), 160.2, 145.2, 119.5 (t, JCF=2.9 Hz), 115.0, 111.6 (t, JCF=243.2 Hz); $^{19}$F-NMR (376 MHz, CDCl$_3$) δ −119.7; IR (neat) ν=2919, 2850, 1583, 1555, 1446, 1383, 1059 cm$^{-1}$; HRMS (ESI-TOF) calc'd for C$_6$H$_4$F$_2$N$_3$ [M+H] 150.0368. found 156.0373.

37-C5: Rf=0.43 (25% EtOAc/hexanes); $^1$H-NMR (600 MHz, CDCl$_3$) δ 9.01 (d, J=1.1 Hz, 2H), 6.84 (t, J=54.7 Hz, 1H); $^{13}$C-NMR (150 MHz, CDCl$_3$) δ 155.9 (t, JCF=5.8 Hz), 146.8, 130.1 (t, JCF=24.4 Hz), 115.2, 111.1 (t, JCF=242.3 Hz); $^{19}$F-NMR (376 MHz, CDCl$_3$) δ −116.0.

1-(2-difluoromethyl)-1-methyl-1H-pyrrol-3-yl)etha-none (38)

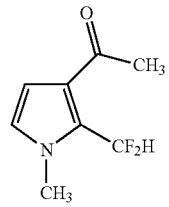

Standard Procedure A (1.0 equiv), zinc salt (2.0-3.0 equiv), TBHP (3.0-5.0 equiv) and $CH_2Cl_2:H_2O$ (2.5:1) at room temperature for a period of 3-12 hours to provide Compound 38 in 65% isolated yield.

Aspects of the Invention:
1. Zinc difluoromethanesulfinate.
2. The zinc difluoromethanesulfinate according to aspect 1 present as a hydrate.
3. The zinc difluoromethanesulfinate according to aspect 2, wherein said hydrate is a trihydrate.
4. A method for difluoromethylating an unsaturated substrate compound that is other than a hydrocarbon compound comprising the steps of:
   a) reacting said unsaturated substrate compound with an excess of zinc difluoromethanesulfinate and an excess of tert-butyl hydroperoxide in a water-containing liquid reaction mixture at an initial temperature below about 10° C. under vigorous agitation; and
   b) permitting said reaction mixture to warm to ambient room temperature, while maintaining said agitation.
5) The method according to aspect 4, wherein said reaction mixture further contains an organic solvent.
6) The method according to aspect 4, wherein said unsaturated substrate compound is a heteroaryl or an α,β-unsaturated compound.
7) The method according to aspect 4, wherein said unsaturated substrate compound and said excess of zinc difluoromethanesulfinate are admixed in a water-containing liquid reaction mixture at an initial temperature below about 10° C. under vigorous agitation prior to the addition of said tert-butyl hydroperoxide, and said tert-butyl hydroperoxide is added slowly thereto.
8) The method according to aspect 4, wherein said zinc difluoromethanesulfinate is a zinc difluoromethanesulfinate hydrate.
9) A method for difluoromethylating an unsaturated substrate compound that is a heteroaryl or an α,β-unsaturated compound comprising the steps of:
   a) providing a first liquid reaction mixture containing i) a water-organic solvent mixture, ii) said unsaturated substrate compound and iii) an excess of zinc difluoromethanesulfinate hydrate at an initial temperature below about 10° C. under vigorous agitation; and
   b) slowly admixing an excess of tert-butyl hydroperoxide to the agitated first reaction mixture to form a second reaction mixture;
   c) permitting said second reaction mixture to warm to ambient room temperature, while maintaining said agitation, to form a difluoromethylated product.
10) The method according to aspect 9, wherein said second reaction mixture is maintained until said unsaturated substrate compound is consumed.
11) The method according to aspect 9, wherein said unsaturated substrate compound that is a heteroaryl compound.
12) The method according to aspect 9, wherein said heteroaryl compound contains 1 to 5 nitrogen atoms in the aromatic ring system that is difluoromethylated.
13) The method according to aspect 9, wherein said difluoromethylated product is collected.
14) The method according to aspect 9, wherein the ratio of zinc difluoromethanesulfinate hydrate to unsaturated substrate in said first reaction mixture is about 2:1 to about 5:1.
15) The method according to aspect 9, wherein the ratio of admixed tert-butyl hydroperoxide to unsaturated substrate is about 3:1 to about 7:1.
16) The method according to aspect 9, wherein the organic solvent in said water-organic solvent mixture is dichloromethane or DMSO.
17) The method according to aspect 10, wherein further amounts of zinc difluoromethanesulfinate hydrate and tert-butyl hydroperoxide are admixed with second reaction mixture if the unsaturated substrate compound is not consumed after about 24 hours.
18) A method of preparing a zinc difluoromethanesulfinate that comprises the steps of:
   a) admixing $HCF_2SO_2Cl$ in a vessel with an agitated admixture of zinc particles and water cooled to about zero degrees C. to form a reaction mixture, moles of said zinc particles being in excess over the moles of $HCF_2SO_2Cl$ admixed;
   b) permitting said reaction mixture to warm to about ambient room temperature;
   c) separating unreacted zinc powder from the remaining reaction mixture; and
   d) removing the water to provide the zinc difluoromethanesulfinate.
19) The method according to aspect 18, wherein the zinc difluoromethanesulfinate formed is a hydrate.
20) The method according to aspect 19, wherein said zinc difluoromethanesulfinate a hydrate contains 1 to 4 water molecules per zinc difluoromethanesulfinate molecule.
21) The method according to aspect 18, wherein said zinc difluoromethanesulfinate is recovered.
22) The method according to aspect 18, wherein said vessel is a pressure vessel that is sealed after admixture of $HCF_2SO_2Cl$ is complete, and while the reaction mixture is permitted to warm to about ambient room temperature.
23) The method according to aspect 18, wherein said reaction mixture is agitated until the $HCF_2SO_2Cl$ has reacted.
24) The method according to aspect 18, wherein the molar ratio of zinc to $HCF_2SO_2Cl$ is about 2:1 to about 10:1.
25) The method according to aspect 18, wherein said zinc particles are sized to pass through sieve of about 1250 to about 2500 Tyler mesh through about 10 to about 18 Tyler mesh.
26) A method of forming a difluoromethyl aromatic thioether product that comprises the steps of:
   a) reacting aromatic thiol substrate compound with an excess of zinc difluoromethanesulfinate and an excess of tert-butyl hydroperoxide in a water-containing liquid reaction mixture at an initial temperature below about 10° C. under vigorous agitation; and
   b) permitting said reaction mixture to warm to ambient room temperature, while maintaining said agitation.
27) The method according to aspect 26, wherein said reaction mixture further contains an organic solvent.

28) The method according to aspect 27, wherein the organic solvent in said water-organic solvent mixture is dichloromethane or DMSO.

29) The method according to aspect 26, wherein said difluoromethyl aromatic thioether product is collected.

30) The method according to aspect 26, wherein said difluoromethyl aromatic thioether product is

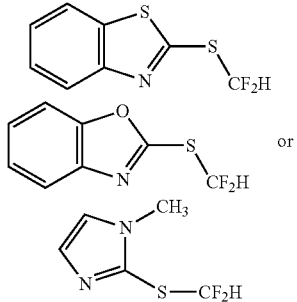

Each of the patents, patent applications and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

The invention claimed is:

1. Zinc difluoromethanesulfinate.

2. The zinc difluoromethanesulfinate according to claim 1 present as a hydrate.

3. The zinc difluoromethanesulfinate according to claim 2, wherein said hydrate is a trihydrate.

4. A method of preparing the zinc difluoromethanesulfinate of claim 1 that comprises the steps of:
   a) admixing $HCF_2SO_2Cl$ in a vessel with an agitated admixture of zinc particles and water cooled to about zero degrees C. to form a reaction mixture, moles of said zinc particles being in excess over the moles of $HCF_2SO_2Cl$ admixed;
   b) permitting said reaction mixture to warm to about ambient room temperature;
   c) separating unreacted zinc powder from the remaining reaction mixture; and
   d) removing the water to provide the zinc difluoromethanesulfinate.

5. The method according to claim 4, wherein the zinc difluoromethanesulfinate formed is a hydrate.

6. The method according to claim 4, wherein said zinc difluoromethanesulfinate is recovered.

7. The method according to claim 4, wherein said vessel is a pressure vessel that is sealed after admixture of $HCF_2SO_2Cl$ is complete, and while the reaction mixture is permitted to warm to about ambient room temperature.

8. The method according to claim 4, wherein said reaction mixture is agitated until the $HCF_2SO_2Cl$ has reacted.

9. The method according to claim 4, wherein the molar ratio of zinc to $HCF_2SO_2Cl$ is about 2:1 to about 10:1.

10. The method according to claim 4, wherein said zinc particles are sized to pass through sieve of about 1250 to about 2500 Tyler mesh through about 10 to about 18 Tyler mesh.

* * * * *